US010501815B2

(12) United States Patent
Cuero Rengifo

(10) Patent No.: US 10,501,815 B2
(45) Date of Patent: *Dec. 10, 2019

(54) GLUCOSE SENSORS AND METHODS OF USE THEREOF

(71) Applicant: INTERNATIONAL PARK OF CREATIVITY, Bogota (CO)

(72) Inventor: Raul Cuero Rengifo, Cypress, TX (US)

(73) Assignee: International Park of Creativity, Bogota (CO)

( * ) Notice: Subject to any disclaimer, the term of this patent is extended or adjusted under 35 U.S.C. 154(b) by 45 days.

This patent is subject to a terminal disclaimer.

(21) Appl. No.: 15/942,681

(22) Filed: Apr. 2, 2018

(65) Prior Publication Data

US 2018/0223379 A1 Aug. 9, 2018

Related U.S. Application Data

(63) Continuation of application No. 15/498,630, filed on Apr. 27, 2017, now Pat. No. 9,932,644, which is a continuation of application No. 14/112,984, filed as application No. PCT/US2012/034170 on Apr. 19, 2012, now Pat. No. 9,683,266.

(60) Provisional application No. 61/478,274, filed on Apr. 22, 2011.

(51) Int. Cl.
| | |
|---|---|
| *C12Q 1/6897* | (2018.01) |
| *C12N 15/81* | (2006.01) |
| *C12N 15/52* | (2006.01) |
| *C12N 1/18* | (2006.01) |
| *G01N 33/66* | (2006.01) |
| *G01N 33/74* | (2006.01) |

(52) U.S. Cl.
CPC .......... *C12Q 1/6897* (2013.01); *G01N 33/66* (2013.01); *G01N 33/74* (2013.01); *G01N 2333/62* (2013.01)

(58) Field of Classification Search
None
See application file for complete search history.

(56) References Cited

U.S. PATENT DOCUMENTS

| | | | |
|---|---|---|---|
| 6,416,959 B1 | 7/2002 | Giuliano et al. | |
| 6,537,806 B1 | 3/2003 | Osborne et al. | |
| 9,683,266 B2 | 6/2017 | Rengifo et al. | |
| 9,932,644 B2 * | 4/2018 | Cuero Rengifo | C12Q 1/6897 |
| 2003/0148421 A1 | 8/2003 | Newgard et al. | |
| 2004/0142356 A1 | 7/2004 | Patterson et al. | |
| 2009/0137543 A1 | 5/2009 | Levine et al. | |
| 2010/0021942 A1 | 1/2010 | Freemont et al. | |
| 2010/0015871 A1 | 6/2010 | Thomas | |
| 2010/0185047 A1 | 7/2010 | Khatib | |
| 2011/0039327 A1 | 2/2011 | Winkler et al. | |
| 2011/0071049 A1 | 3/2011 | Heintz et al. | |

FOREIGN PATENT DOCUMENTS

| | | |
|---|---|---|
| WO | 1996040963 | 12/1996 |
| WO | 2005093075 | 10/2005 |
| WO | 2009037279 | 3/2009 |

OTHER PUBLICATIONS

Goffeau et al. Life with 6000 Genes. Oct. 25, 1996. Science. vol. 274, pp. 546-567. (Year: 1996).*
U.S. Office Action for U.S. Appl. No. 14/112,984 dated Oct. 23, 2015.
Colicelli et al. GenBank Accession CVU33753 [online]. Sep. 19, 1995, downloaded from http://www.ncbi.nlm.nih.gov/nuccore/U33753 on Oct. 21, 2013.
International Search Report and Written Opinion for PCT/US12/34170 dated Nov. 2, 2012.
Muzny et al. GenBank Accession AC094812; May 9, 2003 [online]; downloaded from http://www.ncbi.nlm.nih.gov/nuccore/AC094812 on Oct. 18, 2013.
Ullrich et al. GenBank Accession J00747; Apr. 27, 1883 [online]; downloaded from http://www.ncbi.nlm.nih.gov/nuccore/J00747.
Celenza et al. UniProt Accession P10870; Apr. 5, 2011 [online], downloaded from http://www.uniprot.org/uniprot/P10870 on Oct. 21, 2013.
McNally et al. UniProt Accession P00549; Apr. 5, 2011 [online], dowloaded from http://www.uniprot.org/uniprot/P00549 on Oct. 21, 2013.
Bernstein et al. UniProt Accession P07283; Apr. 5, 2011 [online], dowloaded from http://www.uniprot.org/uniprot/P07283 on Oct. 21, 2013.
Thompson et al. UniProt Accession P17505; Apr. 5, 2011 [online], downloaded from http://www.uniprot.org/uniprot/P17505 on Oct. 21, 2013.
Extended European Search Report for PCT/US2012/034170 dated Mar. 26, 2015.
Szabat et al., "Maturation of adult beta cells revealed using a Pdx1/insulan dual-reporter lentivirus," Endocrinology, 2009, 150:1627-1635.
Kim et al., "A dual-reporter system for specific tracing of pancreatic ss-cell lines that non-invasively measures viable in vivo islet cells," Biotechnology Letters, 2010, 32:53-57.
Ganzlin et al., "In-depth analysts of the Aspergillus niger glucoamylase (glaA) promoter performance using high-throughput screening and controlled bioreactor cultivation techniques," Journal of Biotechnology, 2008, 135:266-271.
Fukuzawa et al., "Development of a novel beta-cell specific promoter system for the identification of insulin-producing cells in in vitro cell cultures," Experimental Cell Research, 2006, 312:3404-3412.
Pedersen et al., "The promoter for the gene encoding the catalytic subunit of rat glucose-6-phosphatase contains two distinct glucose-responsive regions," American Journal of Physiology, Endocrinology and Metabolism, 2007, 292: E788-E801.
Ohtani et al., "Identification and characterization of a glucose-responsiveness region upstream of human insulin gene in transfected HIT-T 15 cells," Biochemical and Biophysical Research Communications, 1998, 242;446-451.

* cited by examiner

*Primary Examiner* — Channing S Mahatan
(74) *Attorney, Agent, or Firm* — Thomas|Horstemeyer, LLP

(57) ABSTRACT

Described herein are glucose and insulin sensors. The sensors are composed of host cells with DNA specifically designed to produce fluorescence when the cells come into contact with glucose and/or insulin in the sample. Once the fluorescence has been quantified, it can be correlated with the amount of glucose and/or insulin present in the sample.

10 Claims, 11 Drawing Sheets

Specification includes a Sequence Listing.

SEQUENCE LISTING

```
<160> NUMBER OF SEQ ID NOS: 36

<210> SEQ ID NO 1
<211> LENGTH: 1445
<212> TYPE: DNA
<213> ORGANISM: Saccharomyces serivisiae

<400> SEQUENCE: 1
aagaaatgat ggtaaatgaa ataggaaatc aaggagcatg aaggcaaaag acaaatataa      60
gggtcgaacg aaaaataaag tgaaaagtgt tgatatgatg tatttggctt tgcggcgccg     120
```

-continued

| | |
|---|---|
| aaaaaacgag tttacgcaat tgcacaatca tgctgactct gtggcggacc cgcgctcttg | 180 |
| ccggcccggc gataacgctg ggcgtgaggc tgtgcccggc ggagttttt gcgcctgcat | 240 |
| tttccaaggt ttaccctgcg ctaaggggcg agattggaga agcaataaga atgccggttg | 300 |
| gggttgcgat gatgacgacc acgacaactg gtgtcattat ttaagttgcc gaaagaacct | 360 |
| gagtgcattt gcaacatgag tatactagaa gaatgagcca agacttgcga gacgcgagtt | 420 |
| tgccggtggt gcgaacaata gagcgaccat gaccttgaag gtgagacgcg cataaccgct | 480 |
| agagtacttt gaagaggaaa cagcaatagg gttgctacca gtataaatag acaggtacat | 540 |
| acaacactgg aaatggttgt ctgtttgagt acgctttcaa ttcatttggg tgtgcacttt | 600 |
| attatgttac aatatggaag ggaactttac acttctccta tgcacatata ttaattaaag | 660 |
| tccaatgcta gtagagaagg ggggtaacac ccctccgcgc tcttttccga ttttttcta | 720 |
| aaccgtggaa tatttcggat atccttttgt tgtttccggg tgtacaatat ggacttcctc | 780 |
| ttttctggca accaaaccca tacatcggga ttcctataat accttcgttg gtctccctaa | 840 |
| catgtaggtg gcggagggga gatatacaat agaaacagata ccagacaaga cataatgggc | 900 |
| taaacaagac tacaccaatt acactgcctc attgatggtg gtacataacg aactaatact | 960 |
| gtagccctag acttgatagc catcatcata tcgaagtttc actacccttt ttccatttgc | 1020 |
| catctattga agtaataata ggcgcatgca acttcttttc tttttttc ttttctctct | 1080 |
| cccccgttgt tgtctcacca tatccgcaat gacaaaaaaa atgatggaag acactaaagg | 1140 |
| aaaaaattaa cgacaaagac agcaccaaca gatgtcgttg ttccagagct gatgaggggt | 1200 |
| atcttcgaac acacgaaact tttccttcc ttcattcacg cacactactc tctaatgagc | 1260 |
| aacggtatac ggccttcctt ccagttactt gaatttgaaa taaaaaagt ttgccgctt | 1320 |
| gctatcaagt ataaatagac ctgcaattat taatcttttg tttcctcgtc attgttctcg | 1380 |
| ttcccttct tccttgtttc tttttctgca caatatttca agctatacca agcatacaat | 1440 |
| caact | 1445 |

<210> SEQ ID NO 2
<211> LENGTH: 2244
<212> TYPE: DNA
<213> ORGANISM: Pichia stipitis

<400> SEQUENCE: 2

| | |
|---|---|
| atgtggaaat ttctagaagc tctactttac gacaacacca tcgaagaaga atactacagg | 60 |
| aaaatccgtc aaaagtcctc ctccaagtcg gctgtaatcg taggtcttgt agctgccgtg | 120 |
| ggaggctttt tgtatgggta cgatacggga ctcatcaacg acttgctaga aatgagatac | 180 |
| gtctacgaaa actttccaga aaatctgcat tcgttcacat cacatgaacg agcgttgatt | 240 |
| acggctgtgt tatcgctcgg aacattcata ggagctctca tagcgcctct tatctccgac | 300 |
| aactatggcc ggaagttttc catcattgtc tcttccggtc tcattttcaa cgcaggcaac | 360 |
| attttgcaaa tcgcatcaac aaacgtagca ttgctttgcg ttggtagagc gatctcgggt | 420 |
| gtatctgtag gcattctttc ggccattgta cccttgtacc aagctgaagc ttctcccaaa | 480 |
| tgggtcagag gttccgtcgt tttcacatat caatgggcca ttacttgggg cttgttgata | 540 |
| gcgagtgccg tctgtcaagg cactcgaaaa atgaccaatt ctggctcata tcggatcccc | 600 |
| gtgggcctcc agtttctctg ggctcttatc ttgtacacgg ggatgctttt cttgcccgaa | 660 |
| agtccccgtt attatgttca aaagacgat cttcagaaag ctctagatag tttgtcgaag | 720 |
| ttgcgaaagt tgcccccaga cgacgctgat ttgatagagg agttggtgga aatcaaggct | 780 |

```
aactacgact acgagttgtc gtatggtaag accaactatc ttgattgctt ccgtagtgga    840
ggaggaagac acaagcaggt gttgcgaatg ttcactggaa tcggtgctca actctttcag    900
cagtgttcag gcatcaactt catcttctac tatggtgtca acttcttctc cagcaccggc    960
atccagaact tttacatcat gtccttcgtg acgtatttgg tcaacactat cttcacaatc   1020
cccggaataa ttctagtgga tacgataggc aggcgacagt tgctcctatg ggtggcgta    1080 ggcatgtcta ccgcgaactt cataattgcg attacgggag tcagtatctc cagtaaggaa   1140
accagttcga ttcaagcgt ctgttttcg tgtgtgttca tagcgttttt cgccagttcg   1200
tggggtggat gtgtatgggc actcacttct gatatatacg gtattagtat cagacagaga   1260
gccatatcca tcactacagc cacgaactgg ttggtcaact tcatctttgc ctacataaca   1320
ccgtatctca tcgatacggg acaccatact gcagctatag aaacaaaat cttctttatc   1380 tggggaggtt gtaacgctgc cggtgtcgtt ttcgtctact tcactgtcta cgaaacaaag   1440
ggattgaagt tggaggaaat tgattatatg tacgctcatt gtgacaatgc gagaaagtcc   1500
accgagttca agtcgaccaa aatcgattac actagattgg acgagaacta caacgctgta   1560
ccctgggatc ctccttatcc atcaacaacg agctcatcgc ctccttctaa catcaacgag   1620
aaggaccttt catcttctga tcccaaccaa gacgtcaatg tacatagtga caacaacgag   1680
tttgttccat tgtacaacaa caaaaaactt ccaaataatc ctacaaacac caacaaaaac   1740
gacatcacca tcattcccta caacaatatc attctgccgt cgttatcatc gaactccgag   1800
ccctcttctg ctgcttcgtc aattctcaac aacagattcc accacaactc tgtctcgact   1860
acaaacaacg tctctgtatc tacatctaac cctggccaat cttctggtca aggtacagct   1920
tccaacgact acttgctgta tttggatagt ttgaagtctg agtacggaag tccacctcac   1980
tacaataacg acacactaca ccagcagcac accaaccaat cgaactccaa gggttctgct   2040
acagacagaa acagcagcat cactgctagc aacattcacc atactcatag caacatcacc   2100
agcaacatta ataaccataa tagtaataac attaataaca gtataaccaa caattcgacc   2160
acgattattg ccacgccata cttcaaccag cctccaccag actcttccga tgaagaagac   2220
gaagacgagg acgaagaaga atag                                          2244

<210> SEQ ID NO 3
<211> LENGTH: 76
<212> TYPE: RNA
<213> ORGANISM: Saccharomyces serivisiae

<400> SEQUENCE: 3
ugcuuaaggc cuaaaacaua ccagaucgcc acccgcgcuu uaaucuggag aggugaauac    60
gaccaccuag gccaaa                                                    76

<210> SEQ ID NO 4
<211> LENGTH: 29
<212> TYPE: DNA
<213> ORGANISM: Artificial sequence
<220> FEATURE:
<223> OTHER INFORMATION: Synthetic Construct
<220> FEATURE:
<221> NAME/KEY: misc_feature
<222> LOCATION: (13)..(15)
<223> OTHER INFORMATION: n is a, c, g, or t
<220> FEATURE:
<221> NAME/KEY: misc_feature
<222> LOCATION: (18)..(20)
<223> OTHER INFORMATION: n is a, c, g, or t
```

<400> SEQUENCE: 4

```
tctagagaaa gannngannn tactagatg                                29
```

<210> SEQ ID NO 5
<211> LENGTH: 129
<212> TYPE: DNA
<213> ORGANISM: Artificial sequence
<220> FEATURE:
<223> OTHER INFORMATION: Synthetic construct

<400> SEQUENCE: 5

```
ccaggcatca ataaaacga aaggctcagt cgaaagactg ggcctttcgt tttatctgtt    60
gtttgtcggt aacgctctc tactagagtc acactggctc accttcgggt gggccttttct  120
gcgtttata                                                         129
```

<210> SEQ ID NO 6
<211> LENGTH: 979
<212> TYPE: DNA
<213> ORGANISM: Artificial sequence
<220> FEATURE:
<223> OTHER INFORMATION: Synthetic construct

<400> SEQUENCE: 6

```
tccctatcag tgatagagat tgacatccct atcagtgata gagatactga gcactactag    60
agaaagagga gaaatactag atggtgagca agggcgagga gctgttcacc ggggtggtgc   120
ccatcctggt cgagctggac ggcgacgtga acggccacaa gttcagcgtg tccggcgagg   180
gcgagggcga tgccacctac ggcaagctga ccctgaagtt catctgcacc accggcaagc   240
tgcccgtgcc ctggcccacc ctcgtgacca ccctgacctg gggcgtgcag tgcttcagcc   300
gctaccccga ccacatgaag cagcacgact tcttcaagtc cgccatgccc gaaggctacg   360
tccaggagcg caccatcttc ttcaaggacg acggcaacta caagacccgc gccgaggtga   420
agttcgaggg cgacaccctg gtgaaccgca tcgagctgaa gggcatcgac ttcaaggagg   480
acggcaacat cctggggcac aagctggagt acaactacat cagccacaac gtctatatca   540
ccgccgacaa gcagaagaac ggcatcaagg ccaacttcaa gatccgccac aacatcgagg   600
acggcagcgt gcagctcgcc gaccactacc agcagaacac ccccatcggc gacggccccg   660
tgctgctgcc cgacaaccac tacctgagca cccagtccgc cctgagcaaa gaccccaacg   720
agaagcgcga tcacatggtc ctgctggagt tcgtgaccgc cgccgggatc actctcggca   780
tggacgagct gtacaagagg cctgctgcaa acgacgaaaa ctacgcttta gtagcttaat   840
aatactagag ccaggcatca ataaaaacga aaggctcagt cgaaagactg ggcctttcgt   900
tttatctgtt gtttgtcggt aacgctctc tactagagtc acactggctc accttcgggt   960
gggccttttct gcgtttata                                             979
```

<210> SEQ ID NO 7
<211> LENGTH: 401
<212> TYPE: DNA
<213> ORGANISM: Rattus norvegicus

<400> SEQUENCE: 7

```
tagaaactat gaaacagttc cagggacaaa gataccaggt ccccaacaac tgcaactttc    60
tgggaaatga ggtggaaaat gctcagccaa ggaaaagag ggccttaccc tctctgggac   120
aatgattgtg ctgtgaactg cttcatcagg ccatctggcc ccttgttaat aatctaatta   180
ccctaggtct aagtagagtt gttgacgtcc aatgagcgct ttctgcagac ttagcactag   240
```

```
gcaagtgttt ggaaattaca gcttcagccc ctctcgccat ctgcctacct accctcccta    300
gagcccttaa tgggccaaac ggcaaagtcc aggggggcaga gaggaggtgc tttggactat    360
aaagctagtg agacccagt aactcccaac cctaagtgac c                        401

<210> SEQ ID NO 8
<211> LENGTH: 333
<212> TYPE: DNA
<213> ORGANISM: Artificial sequence
<220> FEATURE:
<223> OTHER INFORMATION: Synthetic construct

<400> SEQUENCE: 8
atggcgctgt ggatgcgcct gttaccgctg ttagcgctgc tggcactgtg ggggcctgat    60
ccggcggcag cttttgtgaa tcagcacctg tgcggtagtc atctggtcga agccctgtat   120
ctggtgtgcg gtgaacgtgg gttttttctat acgccgaaaa ctcgccggga ggccgaggac   180
ctgcaggttg gtcaggtaga actgggcggt ggtccaggcg ccggctcact gcagccgctg   240
gctctggagg gcagcttaca aaagcgtggc atcgttgaac aatgttgcac ctccatttgt   300
tctttatacc agttagaaaa ctactgtaac taa                                333

<210> SEQ ID NO 9
<211> LENGTH: 27
<212> TYPE: DNA
<213> ORGANISM: Artificial sequence
<220> FEATURE:
<223> OTHER INFORMATION: Synthetic construct (5' to 3')

<400> SEQUENCE: 9
ttcgaaatcc tagaaactat gaaacag                                        27

<210> SEQ ID NO 10
<211> LENGTH: 23
<212> TYPE: DNA
<213> ORGANISM: Artificial sequence
<220> FEATURE:
<223> OTHER INFORMATION: Synthetic construct (5' to 3')

<400> SEQUENCE: 10
ggatccggtc acttagggtt ggg                                            23

<210> SEQ ID NO 11
<211> LENGTH: 32
<212> TYPE: DNA
<213> ORGANISM: Artificial sequence
<220> FEATURE:
<223> OTHER INFORMATION: Synthetic construct (5' to 3')

<400> SEQUENCE: 11
ggtaccttct ttcgatggta aatgaaatag ga                                  32

<210> SEQ ID NO 12
<211> LENGTH: 23
<212> TYPE: DNA
<213> ORGANISM: Artificial sequence
<220> FEATURE:
<223> OTHER INFORMATION: Synthetic construct (5' to 3')

<400> SEQUENCE: 12
ggatccagtt gattgtatgc ttg                                            23
```

```
<210> SEQ ID NO 13
<211> LENGTH: 23
<212> TYPE: DNA
<213> ORGANISM: Artificial sequence
<220> FEATURE:
<223> OTHER INFORMATION: Synthetic construct (5' to 3')

<400> SEQUENCE: 13
ctcgaggtga tagagattga cat                                               23

<210> SEQ ID NO 14
<211> LENGTH: 30
<212> TYPE: DNA
<213> ORGANISM: Artificial sequence
<220> FEATURE:
<223> OTHER INFORMATION: Synthetic construct (5' to 3')

<400> SEQUENCE: 14
tctagaaacg cagaaaggcc cacccgaagg                                        30

<210> SEQ ID NO 15
<211> LENGTH: 32
<212> TYPE: DNA
<213> ORGANISM: Artificial sequence
<220> FEATURE:
<223> OTHER INFORMATION: Synthetic construct (5' to 3')

<400> SEQUENCE: 15
ctcgagttct ttcgatggta aatgaaatag ga                                     32

<210> SEQ ID NO 16
<211> LENGTH: 23
<212> TYPE: DNA
<213> ORGANISM: Artificial sequence
<220> FEATURE:
<223> OTHER INFORMATION: Synthetic construct (5' to 3')

<400> SEQUENCE: 16
tctagactat tcttcttcgt cct                                               23

<210> SEQ ID NO 17
<211> LENGTH: 23
<212> TYPE: DNA
<213> ORGANISM: Artificial sequence
<220> FEATURE:
<223> OTHER INFORMATION: Synthetic construct (5' to 3')

<400> SEQUENCE: 17
tctagattat aaacgcagaa agg                                               23

<210> SEQ ID NO 18
<211> LENGTH: 23
<212> TYPE: DNA
<213> ORGANISM: Artificial sequence
<220> FEATURE:
<223> OTHER INFORMATION: Synthetic construct (5' to 3')

<400> SEQUENCE: 18
ctcgagggat tcaaagagga gaa                                               23

<210> SEQ ID NO 19
<211> LENGTH: 23
<212> TYPE: DNA
<213> ORGANISM: Artificial sequence
<220> FEATURE:
<223> OTHER INFORMATION: Synthetic construct (5' to 3')
```

<400> SEQUENCE: 19

```
tctagattat aaacgcagaa agg                                           23
```

<210> SEQ ID NO 20
<211> LENGTH: 1155
<212> TYPE: DNA
<213> ORGANISM: Saccharomyces cerevisiae

<400> SEQUENCE: 20

```
atgtccaaga gcaaaacttt cttatttacc tctgaatccg tcggtgaagg tcacccagac    60
aagatttgtg accaagtttc tgatgctatt ttggacgctt gtttagaaca agatccattc   120
tccaaggttg cctgtgaaac agctgccaaa actggtatga ttatggtttt cggtgaaatt   180
accaccaaag ctagacttga ctaccaacaa atagtaagag ataccatcaa gaagattggt   240
tatgacgatt ctgccaaggg tttcgactac aagacatgta atgttttagt agctatcgaa   300
caacaatctc cagatatcgc tcaaggtctg cactatgaaa agagcttaga agacttaggt   360
gctggtgacc aaggtataat gtttggttac gctacagacg aaactccaga agggttacca   420
ttgaccattc ttttggctca caattgaac atggctatgg cagatgctag aagagatggt   480
tctctcccat ggttgagacc agacacaaag actcaagtca ctgtcgaata cgaagacgac   540
aatggtagat gggttccaaa gaggatagat accgttgtta tttctgctca acatgctgat   600
gaaatttcca ccgctgactt gagaactcaa cttcaaaaag atattgttga aaaggtcata   660
ccaaaggata tgttagacga aaataccaaa tatttcatcc aaccatccgg tagattcgtc   720
atcggtggtc ctcaaggtga cgctggtttg accggtagaa agattattgt cgacgcttac   780
ggtggtgcct catccgtcgg tggtggtgcc ttctccggta aggactattc caaggtcgat   840
cgttccgctg cttacgctgc tagatgggtt gccaagtctc tagttgccgc tggtttgtgt   900
aagagagtcc aagtccaatt ttcatatgct attggtattg ctgaaccatt gtctttacat   960
gtggacacct atggtacagc tacaaaatca gatgacgaaa tcattgaaat tattaagaag  1020
aacttcgact tgagaccagg tgtgttagta aaggaattag atttggctag accaatttac  1080
ttaccaaccg cttcttatgg tcacttcact aatcaagagt actcatggga aaaccaaag   1140
aaattggaat tttaa                                                   1155
```

<210> SEQ ID NO 21
<211> LENGTH: 1503
<212> TYPE: DNA
<213> ORGANISM: Saccharomyces cerevisiae

<400> SEQUENCE: 21

```
atgtctagat tagaaagatt gacctcatta aacgttgttg ctggttctga cttgagaaga    60
acctccatca ttggtaccat cggtccaaag accaacaacc cagaaacctt ggttgctttg   120
agaaaggctg gtttgaacat tgtccgtatg aacttctctc acggttctta cgaataccac   180
aagtctgtca ttgacaacgc cagaaagtcc gaagaattgt acccaggtag accattggcc   240
attgctttgg acaccaaggg tccagaaatc agaactggta ccaccaccaa cgatgttgac   300
tacccaatcc caccaaacca cgaaatgatc ttcaccaccg atgacaagta cgctaaggct   360
tgtgacgaca agatcatgta cgttgactac aagaacatca ccaaggtcat ctccgctggt   420
agaatcatct acgttgatga tggtgttttg tctttccaag ttttggaagt cgttgacgac   480
aagactttga aggtcaaggc tttgaacgcc ggtaagatct gttccacaa gggtgtcaac   540
ttaccaggta ccgatgtcga tttgccagct ttgtctgaaa aggacaagga agatttgaga   600
```

```
ttcggtgtca agaacggtgt ccacatggtc ttcgcttctt tcatcagaac cgccaacgat        660
gttttgacca tcagagaagt cttgggtgaa caaggtaagg acgtcaagat cattgtcaag        720
attgaaaacc aacaaggtgt taacaacttc gacgaaatct tgaaggtcac tgacggtgtt        780
atggttgcca gaggtgactt gggtattgaa atcccagccc cagaagtctt ggctgtccaa        840
aagaaattga ttgctaagtc taacttggct ggtaagccag ttatctgtgc tacccaaatg        900
ttggaatcca tgacttacaa cccaagacca ccagagctg aagtttccga tgtcggtaac         960
gctatcttgg atggtgctga ctgtgttatg ttgtctggtg aaaccgccaa gggtaactac       1020
ccaatcaacg ccgttaccac tatggctgaa accgctgtca ttgctgaaca agctatcgct       1080
tacttgccaa actacgatga catgagaaac tgtactccaa agccaacctc caccaccgaa       1140
accgtcgctg cctccgctgt cgctgctgtt ttcgaacaaa aggccaaggc tatcattgtc       1200
ttgtccactt ccggtaccac cccaagattg gtttccaagt acagaccaaa ctgtccaatc       1260
atcttggtta ccagatgccc aagagctgct agattctctc acttgtacag aggtgtcttc       1320
ccattcgttt tcgaaaagga acctgtctct gactggactg atgatgttga agcccgtatc       1380
aacttcggta ttgaaaaggc taaggaattc ggtatcttga agaagggtga cacttacgtt       1440
tccatccaag gtttcaaggc cggtgctggt cactccaaca ctttgcaagt ctctaccgtt       1500
taa                                                                     1503

<210> SEQ ID NO 22
<211> LENGTH: 765
<212> TYPE: DNA
<213> ORGANISM: Saccharomyces cerevisiae

<400> SEQUENCE: 22
atgagtatcg ctgaattcgc ttacaaggaa aaaccagaaa ctttggtttt attcgatgtt         60
gatggtacct tgacaccagc cagattaact gtttctgaag aagttagaaa aactttggcc        120
aagttgagaa acaagtgctg cattggtttt gtcggtggtt ctgacttaag caagcaatta        180
gaacagttag gcccaaacgt tttagatgaa tttgactatt cttctctga aatggtttg          240
accgcctaca gattaggtaa ggaattagct tctcaatcct tcatcaactg gctcggtgag        300
gaaaaataca ataaattggc cgtcttcatt ttgagatatc tatctgaaat tgacttgcca        360
aagagaagag gtacttttct tggaatttaga aatggtatga tcaacgtttc cccaattggt       420
agaaatgctt ctactgagga aagaaacgaa ttcgaaagat acgataagga acaccaaatc        480
agagccaagt tcgttgaagc tttgaaaaag gaattcccag actacggttt gactttctcc        540
attggtggcc aaatctcttt cgacgttttc cccgctggtt gggataagac ctactgtttg        600
caacacgttg aaaagatgg tttcaaggaa attcatttct tggtgacaa gactatggtc          660
ggtggtaacg attacgaaat ttttgtcgat gaaagaacca tcggacattc agtacaatcc        720
cctgatgaca ccgtcaaaat tttgactgaa ctattcaact tatag                        765

<210> SEQ ID NO 23
<211> LENGTH: 1005
<212> TYPE: DNA
<213> ORGANISM: Saccharomyces cerevisiae

<400> SEQUENCE: 23
atgttgtcaa gagtagctaa acgtgcgttt tcctctacag ttgccaaccc ttataaagtg         60
actgttttgg gtgcaggcgg tggtattgga caaccattgt ctttgcttct aaagcttaac        120
cataaagtca cggacttaag actgtacgac ctaaagggcg caaaaggtgt tgccaccgat        180
```

```
ttgtctcata ttccaacaaa ctccgtggtc aagggggttta ctccagaaga gccagacgga      240
ttgaacaacg ctttaaagga cacagacatg gttttaattc ctgctggtgt gcccagaaag      300
cctggtatga cacgtgatga cttgttcgcc atcaacgcaa gcatcgttcg cgatttggca      360
gcagcaaccg ccgaatccgc tcccaatgct gccattctgg tcatttccaa cccagtcaat      420
tctaccgttc caattgtcgc ccaagtcttg aaaaacaagg gtgtttacaa cccaaagaaa      480
ttgttcggtg tgactacctt ggactctatt agagccgcca gattcatctc agaagtcgag      540
aacaccgatc caactcagga aagggttaac gtcatcggtg gacattctgg tattaccatc      600
atcccattga tttcgcaaac aaaccataag ttgatgtctg atgacaagag acacgaattg      660
attcacagaa tacagtttgg tggtgacgaa gtcgtcaaag caaagaatgg tgctggctct      720
gctacgttgt caatggccca tgctggtgct aaattcgcta acgctgtttt gtccggtttc      780
aaaggcgaaa gagacgtcat cgagccttcc ttcgtggact ctcccttgtt caaatccgaa      840
ggcatcgaat tctttgcatc tccggtcact ttgggcccag atggtattga aaagatccat      900
ccaataggtg agttatcttc agaagaagaa gaaatgctac aaaaatgtaa agaaaccttg      960
aagaagaata tcgaaaaggg tgtcaacttt gttgctagta aatag                      1005

<210> SEQ ID NO 24
<211> LENGTH: 1458
<212> TYPE: DNA
<213> ORGANISM: Saccharomyces cerevisiae

<400> SEQUENCE: 24
atggttcatt taggtccaaa gaaaccacag gctagaaagg gttccatggc tgatgtgccc       60
aaggaattga tggatgaaat tcatcagttg gaagatatgt ttacagttga cagcgagacc      120
ttgagaaagg ttgttaagca ctttatcgac gaattgaata aaggtttgac aaagaaggga      180
ggtaacattc caatgattcc cggttgggtc atggaattcc aacaggtaa agaatctggt      240 aactatttgg ccattgattt gggtggtact aacttaagag tcgtgttggt caagttgagc      300
ggtaaccata cctttgacac cactcaatcc aagtataaac taccacatga catgagaacc      360
actaagcacc aagaggagtt atggtccttt attgccgact cttttgaagga ctttatggtc      420 gagcaagaat tgctaaacac caaggacacc ttaccattag gtttcacctt ctcgtaccca      480
gcttcccaaa acaagattaa cgaaggtatt ttgcaaagat ggaccaaggg tttcgatatt      540
ccaaatgtcg aaggccacga tgtcgtccca ttgctacaaa acgaaatttc caagagagag      600
ttgcctattg aaattgtagc attgattaat gatactgttg gtacttttaat tgcctcatac      660 tacactgacc cagagactaa gatgggtgtg attttcggta ctggtgtcaa cggtgctttc      720
tatgatgttg tttccgatat cgaaaagttg gagggcaaat tagcagacga tattccaagt      780
aactctccaa tggctatcaa ttgtgaatat ggttccttcg ataatgaaca tttggtcttg      840
ccaagaacca agtacgatgt tgctgtcgac gaacaatctc caagacctgg tcaacaagct      900
tttgaaaaga tgacctccgg ttactacttg ggtgaattgt tgcgtctagt gttacttgaa      960
ttaaacgaga agggcttgat gttgaaggat caagatctaa gcaagttgaa acaaccatac     1020
atcatggata cctcctaccc agcaagaatc gaggatgatc catttgaaaa cttggaagat     1080
actgatgaca tcttccaaaa ggactttggt gtcaagacca ctctgccaga acgtaagttg     1140
attagaagac tttgtgaatt gatcggtacc agagctgcta gattagctgt ttgtggtatt     1200
gccgctattt gccaaaagag aggttacaag actggtcaca ttgccgctga cggttctgtc     1260
tataacaaat acccaggttt caaggaagcc gccgctaagg gtttgagaga tatctatgga     1320
```

```
tggactggtg acgcaagcaa agatccaatt acgattgttc cagctgagga tggttcaggt   1380
gcaggtgctg ctgttattgc tgcattgtcc gaaaaaagaa ttgccgaagg taagtctctt   1440
ggtatcattg gcgcttaa                                                  1458

<210> SEQ ID NO 25
<211> LENGTH: 468
<212> TYPE: DNA
<213> ORGANISM: Hordeum vulgare

<400> SEQUENCE: 25
atgctcgtgt accaggacaa gctttccggc gatgaactcc tgtcggattc cttcccgtac     60
agggagctgg agaacggtgt gctctgggaa gtcgatggcc attgggtcgt tcaaggagca    120
gttgatgtgg acattggtgc caacccctct gctgagggtg gtggtgagga tgagggtgtc    180
gatgaccagg ccgtgaaggt ggttgacatt gttgacacct tccgtcttca ggagcaacct    240
gcttttgaca agaagcagtt tattgcttac atcaagcgct acatcaagaa cctcactgcc    300
aagcttgaag gtgaggagct agatgctttc aagaagaacg ttgagtctgc cacgaagtat    360
cttcttagca agctcaagga ccttcagttc tttgtgggcg agagcatgca tgatgatggc    420
agcgtggtgt ttaagcttga ttgcctacta cagggaggga gctgctga                468

<210> SEQ ID NO 26
<211> LENGTH: 6438
<212> TYPE: DNA
<213> ORGANISM: Saccharomyces cerevisiae

<400> SEQUENCE: 26
atgccagtgt tgaaatcaga caatttcgat ccattggaag aagcttacga aggtgggaca     60
attcaaaact ataacgatga acaccatctt cataaatctt gggcaaatgt gattccggac    120
aaacgaggac tttacgaccc tgattatgaa catgacgctt gtggtgtcgg tttcgtagca    180
aataagcatg gtgaacagtc tcacaagatt gttactgacg ctagatatct tttagtgaat    240
atgacacatc gtggtgccgt ctcatctgat gggaacggtg acggtgccgg tattctgcta    300
ggtattcctc acgaatttat gaaaagagaa ttcaagttag atcttgatct agacatacct    360
gagatgggca aatacgccgt aggtaacgtc ttcttcaaga agaacgaaaa aaataacaag    420
aaaaatttaa ttaagtgtca gaagattttc gaggatttag ctgcatcctt caacttatcc    480
gtattaggtt ggagaaacgt ccccgtagat tctactattt taggagacgt tgcattatct    540
cgtgaaccta ctattctaca gccattattg gttccattgt atgatgaaaa acaaccggag    600
tttaatgaaa ctaaatttag aactcaattg tatcttttaa ggaaggaggc ctctcttcaa    660
ataggactgg aaaactggtt ctatgtttgt tccctaaaca ataccaccat tgtttacaag    720
ggtcaattga cgccagctca agtgtataac tactatcccg acttgactaa tgcgcatttc    780
aaatcccaca tggcgttggt ccattcaaga ttttccacta atactttccc ctcttgggat    840
agagctcaac ctttacgttg gctagctcat aatggtgaaa ttaacacctt aagaggtaac    900
aagaattgga tgcgctccag agaaggtgtg atgaattcag caactttcaa agatgagtta    960
gacaaactat acccaattat cgaagaaggt ggttctgatt cagctgcatt ggataacgtt   1020
ttagaactat tgactattaa tggcacatta tctctacctg aagctgttat gatgatggtt   1080
cctgaagcgt atcataagga tatggattct gacctaaaag catggtacga ctgggctgca   1140
tgtctgatgg aaccttggga tggtccagct ttgttaactt tcactgatgg acgttactgt   1200
ggtgctatat tggatagaaa tggtttaaga ccttgtcgtt attacatcac tagtgatgac   1260
```

```
agagttatct gtgcttcaga ggtaggtgtc attcctatcg aaaattcatt ggttgttcaa      1320
aaaggtaaac tgaagccagg tgatttattc ctagtggata ctcaattggg tgaaatggtc      1380
gatactaaaa agttaaaatc tcaaatctca aaaagacaag attttaagtc ttggttatcc      1440
aaagtcatca agttagacga cttgttatca aaaccgcta atttggttcc taaagaattt       1500
atatcacagg attcattgtc tttgaaagtt caaagtgacc cacgtctatt ggccaatggt      1560
tataccttcg aacaagtcac atttctgtta actccaatgg ctttaacagg taaagaagct      1620
ttaggttcga tgggtaacga tgcgccactg gcttgtttaa atgaaaatcc tgtcttactt      1680
tatgattatt tcagacaatt gtttgctcaa gtgaccaatc ctccaattga cccaattcgt      1740
gaagcaaatg ttatgtcgtt agaatgttat gtcggacctc aaggcaacct tttggaaatg      1800
cattcatctc aatgtgatcg tttattattg aaatctccta ttttgcattg gaatgagttc      1860
caagctttga aaaacattga agctgcttac ccatcatggt ctgtagcaga aattgatatc      1920
acattcgaca agagtgaggg tctattgggc tataccgaca caattgataa aatcactaag      1980
ttagcgagcg aagcaattga tgatggtaaa agatcttaa taattactga caggaaaatg      2040
ggtgccaacc gtgttttccat ctcctctttg attgcaattt catgtattca tcatcccta    2100 atcagaaaca agcagcgttc ccaagttgct ttgattttgg aaacaggtga agccagagaa      2160
attcaccatt tctgtgtcct actaggttat ggttgtgatg gtgtttatcc atacttagcc      2220
atggaaactt tggtcagaat gaatagagaa ggtctacttc gtaatgtcaa caatgacaat      2280
gatacacttg aggaagggca aatactagaa aattacaagc acgctattga tgcaggtatc      2340
ttgaaggtta tgtctaaaat gggtatctcc actctagcat cctacaaagg tgctcaaatt      2400
tttgaagccc taggtttaga taactctatt gttgatttgt gtttcacagg tacttcttcc      2460
agaattagag gtgtaacttt cgagtatttg gctcaagatg cctttctttt acatgagcgt      2520
ggttatccat ccagacaaac cattagtaaa tctgttaact taccagaaag tggtgaatac      2580
cactttaggg atggtggtta caaacacgtc aacgaaccaa ccgcaattgc ttcgttacaa      2640
gatactgtca gaaacaaaaa tgatgtctct tggcaattat atgtaaagaa ggaaatggaa      2700
gcaattagag actgtacact aagaggactg ttagaattag attttgaaaa ttctgtcagt      2760
atccctctag aacaagttga accatggact gaaattgcca gaagatttgc gtcaggtgca      2820
atgtcttatg gttctatttc tatggaagct cactctacat ggctattgc catgaatcgt       2880 ttaggggcca aatccaattg tggtgaaggt ggtgaagacg cagaacgttc tgctgttcaa      2940
gaaaacggtg atactatgag atctgctatc aaacaagttg cttccgctag attcggtgta      3000
acttcatact acttgtcaga tgctgatgaa atccaaatta agattgctca gggtgctaag      3060
ccgggtgaag gtggtgaact accagcccac aaagtgtcta aggatatcgc aaaaaccagg      3120
cactccaccc ctaatgttgg gttaatctct cctcctcctc atcacgatat ttattccatt      3180
gaagatttga acaactgat ttatgatttg aaatgtgcta atccaagagc gggaatttct      3240
gtaaagttgg tttccgaagt tggtgttggt attgttgcct ctggtgtagc taaggctaaa      3300
gccgatcata tcttagtttc tggtcatgat ggtggtacag gtgctgcaag atggacgagt      3360
gtcaaatatg cggttttgcc atgggaatta ggtctagctg aaactcacca gactttagtc      3420
ttgaatgatt taagacgtaa tgttgttgtc caaaccgatg gtcaattgag aactgggttt      3480
gatattgctg ttgcagtttt attaggggca gaatcttta ccttggcaac agttccatta      3540
attgctatgg gttgtgttat gttaagaaga tgtcacttga actcttgtgc tgttggtatt      3600
gccacacaag atccatattt gagaagtaag tttaagggtc agcccgaaca tgttatcaac      3660
```

```
ttcttctatt acttgatcca agatttaaga caaatcatgg ccaagttagg attccgtacc    3720
attgacgaaa tggtgggtca ttctgaaaaa ttaaagaaaa gggacgacgt aaatgccaaa    3780
gccataaata tcgatttatc tcctattttg accccagcac atgttattcg tccaggtgtt    3840
ccaaccaagt tcactaagaa acaagaccac aaactccaca cccgtctaga taataagtta    3900
atcgatgagg ctgaagttac tttggatcgt ggcttaccag tgaatattga cgcctctata    3960
atcaatactg atcgtgcact cggttctact ttatcttaca gagtctcgaa gaaatttggt    4020
gaagatggtt tgccaaagga caccgttgtc gttaacatag aaggttcagc gggtcaatct    4080
tttggtgctt tcctagcttc tggtatcact tttatcttga atggtgatgc taatgattat    4140
gttggtaaag gtttatccgg tggtattatt gtcattaaac caccaaagga ttctaaattc    4200
aagagtgatg aaaatgtaat tgttggtaac acttgtttct atggtgctac ttctggtact    4260
gcattcattt caggtagtgc cggtgagcgt ttcggtgtca gaaactctgg tgccaccatc    4320
gttgttgaga gaattaaggg taacaatgcc tttgagtata tgactggtgg tcgtgccatt    4380
gtcttatcac aaatggaatc cctaaacgcc ttctctggtg ctactggtgg tattgcatac    4440
tgtttaactt ccgattacga cgattttgtt ggaaagatta acaaagatac tgttgagtta    4500
gaatcattat gtgacccggt cgagattgcg tttgttaaga atttgatcca ggagcattgg    4560
aactacacac aatctgatct agcagccagg attctcggta atttcaacca ttatttgaaa    4620
gatttcgtta aagtcattcc aactgattat aagaaagttt tgttgaagga gaaagcagaa    4680
gctgccaagg caaaggctaa ggcaacttca gaatacttaa agaagtttag atcgaaccaa    4740
gaagttgatg acgaagtcaa tactctattg attgctaatc aaaaagctaa agagcaagaa    4800
aaaagaaga gtattactat ttcaaataag gccactttga aggagcctaa ggttgttgat    4860
ttagaagatg cagttccaga ttccaaacag ctagagaaga tagcgaaag gattgaaaaa    4920
acacgtggtt ttatgatcca caaacgtcgt catgagacac acagagatcc aagaaccaga    4980
gttaatgact ggaaagaatt tactaaccct attaccaaga aggatgccaa atatcaaact    5040
gcgagatgta tggattgtgg tacaccattc tgtttatctg ataccggttg tccctatct    5100
aacattatcc ccaagtttaa tgaattgtta ttcaagaacc aatggaagtt ggcactggac    5160
aaattgctag agacaaacaa tttcccagaa ttcactggaa gagtatgtcc agcaccctgt    5220
gagggagctt gtacactagg tattattgaa gacccagtcg gcataaaatc ggttgaaaga    5280
attatcattg acaatgcttt caaggaagga tggattaagc cttgtccacc aagtacacgc    5340
actggcttta cagtgggtgt cattggttct ggtccagcag gtttagcgtg tgctgatatg    5400
ttgaaccgtg ccggacatac ggtcactgtt tatgaaagat ccgaccgttg tggtgggtta    5460
ttgatgtatg gtattccaaa catgaagttg gataaggcta tagtgcaacg tcgtattgat    5520
ctattgagtg ccgaaggtat tgactttgtt accaacaccg aaattggtaa aaccataagc    5580
atggatgagc taagaacaa gcacaatgca gtagtgtatg ctatcggttc taccattcca    5640
cgtgacttac ctattaaggg tcgtgaattg aagaatattg attttgccat gcagttgttg    5700
gaatctaaca caaaagcttt attgaacaaa gatctggaaa tcattcgtga aaagatccaa    5760
ggtaagaaag taattgttgt cggtggtggt gacacaggta acgattgttt aggtacatct    5820
gtaagacacg gtgcagcatc agttttgaat ttcgaattgt tgcctgagcc accagtggaa    5880
cgtgccaaag acaatccatg gcctcaatgg ccgcgtgtca tgagagtgga ctacggtcat    5940
gctgaagtga aagagcatta tggtagagac cctcgtgaat actgcatctt gtccaaggaa    6000
tttatcggta acgatgaggg tgaagtcact gccatcagaa ctgtgcgcgt agaatggaag    6060
```

```
aagtcacaaa gtggcgtatg gcaaatggta gaaattccca acagtgaaga gatctttgaa      6120
gccgatatca ttttgttgtc tatgggtttc gtgggtcctg aattgatcaa tggcaacgat      6180
aacgaagtta agaagacaag acgtggtacg attgccacac tcgacgactc ctcatactct      6240
attgatggag gaaagacttt tgcatgtggt gactgtagaa gagggcaatc tttgattgtc      6300
tgggccatcc aagaaggtag aaaatgtgct gcctctgtcg ataagttcct aatggacggc      6360
actacgtatc taccaagtaa tggtggtatc gttcaacgtg attacaaact attgaaagaa      6420
ttagctagtc aagtctaa                                                    6438

<210> SEQ ID NO 27
<211> LENGTH: 2409
<212> TYPE: DNA
<213> ORGANISM: Saccharomyces cerevisiae

<400> SEQUENCE: 27
atgctcaaca ttctcgtttt aggaaacggt gcaagagaac acgttcttgt caccaagctg        60
gctcagtcac ccaccgtggg taagatctat gtcgctccag gtaatggagg gaccgcaacc       120
atggatcctt cgcgtgtgat aaactgggat attacgccag atgtcgccaa ttttgctcgt       180
ttgcagtcga tggctgtgga acataagatc aacttggtcg ttcctggtcc agaattacct       240
ctagtcaacg gcatcacctc cgtgttccat agcgttggta ttcccgtttt tggaccttcc       300
gtcaaagccg ctcagttgga agcttccaag gctttctcca agagatttat gtcaaaacac       360
aatattccaa ccgcgtctta tgatgtcttc actaatccag aagaagccat ttcattcttg       420
caagctcata ctgacaaagc ttttgtcatc aaggccgacg ggatcgctgc tgggaaaggt       480
gttattatcc catctagcat cgacgagtcc gtccaagcta tcaaggacat aatggtcacc       540
aagcaattcg gtgaagaagc gggcaagcag gttgtgatga acaattctt ggaaggtgat       600 gaaatctctc tactcaccat tgttgacggg tactctcact tcaatctccc cgtcgcacaa       660
gatcacaaga ggatctttga tggcgacaag ggcttgaaca ccggtgggat gggtgcctat       720
gcccccgctc ctgtggccac accatctttg ttgaagacca tagattcaca gattgtgaag       780
cctacgattg atgggatgag acgtgatggt atgccctttg ttggtgtgct gttcaccggg       840
atgattttgg tgaaggattc taagacaaat caacttgttc ccgaagtgtt agaatataat       900
gtcagattcg gtgacccaga gacacaggct gttttgagtt tacttgatga tcaaaccgat       960
ttggcgcaag tgttttggc tgctgctgaa catcgtttgg attccgtaaa cataggaatc      1020
gatgacacaa gatctgccgt tactgtcgta gtggctgcag gtggttatcc tgaatcatac      1080
gccaaaggtg acaaaattac cttggatacc gataaattac ctccacatac acaaatcttc      1140
caagcaggta ccaaatacga ttccgccacc gattctttat tgaccaatgg tggtagagtt      1200
ctttctgtga cctccactgc tcaggacttg agaacagcag tagatacagt atatgaagcc      1260
gtcaaatgcg tccatttcca aaattcttac tacagaaagg acatcgcata ccgtgcgttc      1320
caaaactcag aatcatcaaa agttgccatc acatacgcag actcaggtgt ctctgttgat      1380
aatggtaaca atctcgtaca aactatcaaa gaaatggtca gatccacaag aaggccaggt      1440
gcagactctg atattggtgg ttttggtggt ttattcgatt tggctcaagc aggtttccgt      1500
caaaacgaag ataccttact agtaggtgct acagatggtg tcggtactaa attaatcatt      1560
gcccaagaga ccgggattca taatactgtc ggtattgacc tggtggccat gaatgttaac      1620
gatttggtgg tacaaggtgc tgagcctcta ttcttttgg actactttgc cactggtgct      1680
cttgacattc aagttgcctc tgattttgtg tccggtgttg ctaatggttg tattcaaagt      1740
```

-continued

| | |
|---|---|
| ggttgtgctc ttgtgggtgg tgaaacttcg gaaatgcccg gtatgtatcc acccggccac | 1800 |
| tacgatacta atggtaccgc tgttggtgct gtattaagac aagatatctt gcccaagata | 1860 |
| aatgaaatgg ccgcaggaga tgttcttctg ggtctcgcct ctagcggtgt tcattctaat | 1920 |
| ggtttctctt tggttagaaa aattattcaa catgtagcat taccatggga cgctccatgt | 1980 |
| ccatgggatg aatctaagac gttaggtgaa ggtattcttg aaccaacaaa aatttacgtc | 2040 |
| aagcaattat tgccatcaat tagacaaaga ctactactag gtttagctca tataacaggt | 2100 |
| ggtggtttag tagagaatat cccaagagct attccagacc acctacaggc ccgcgttgat | 2160 |
| atgtcaacct gggaagtacc ccgtgtcttc aaatggtttg gtcaagcagg taatgttcca | 2220 |
| cacgatgaca ttttaagaac cttcaacatg ggtgttggta tggttttgat tgtcaagaga | 2280 |
| gaaaacgtca aggctgtttg tgattcattg actgaagaag gtgaaattat ttgggagctt | 2340 |
| ggttctttgc aagaaagacc aaaggatgct cccggttgtg tgattgaaaa cggaactaag | 2400 |
| ctttactaa | 2409 |

<210> SEQ ID NO 28
<211> LENGTH: 13047
<212> TYPE: DNA
<213> ORGANISM: Mus musculus

<400> SEQUENCE: 28

| | |
|---|---|
| cggttcacta gaggagggaa gaagtctaca aggacccatc aatttcctgc ctgcctgcag | 60 |
| caaggacaga cggcatgagc actgcgggaa aagtaaggaa aagatctcac tgttggaaat | 120 |
| gtattctcag taatacgtgg agagatgcag agtcctacct tagaaataac aggctctgat | 180 |
| ctgctgtagt gcagaaggtg tcctgggtga gcacagcttg acctgctact aaatatcttt | 240 |
| aacaagaggg catagaacct gggtttgtga agtctttat tccctcactt cctctgcagg | 300 |
| acagggaact tattccaagt cagtggtggc tgctttgcaa acagaaagtt tttaaaaagg | 360 |
| tcttttactg aaagtctgta tttatcaata atgtgttatt cttttctggtc atattttgtt | 420 |
| atgaacatag aaaagttaaa tctggcaaga gtttcatagg aggaatttga ttcagggagc | 480 |
| ttagtactgt tcctgtagcc attaggtaac gtttctggtg agagatggac tgatttgaaa | 540 |
| gcattagagt cattcacagt aagattatgt taccatgtaa attgtgattt gaagggccca | 600 |
| ttattgcaca actcacggat ttctacaaaa atccctataaa cagtctctct cctgtttaaa | 660 |
| aaaaaatcat ccagatttta tggaaaatta atttgaataa aaatggaact gattgttagt | 720 |
| attaagaata cacacatatg gtactgagtt ttccacaaaa atcacactca tttgttcagc | 780 |
| gtttacatgg taccgcaatg atggtgaaca gccaatcagt ataattaatt atctatcgct | 840 |
| taattatata agcctatgtt tctgttggca cagaggctat tttaggagtg ggtcaagagt | 900 |
| ccaacaactg acagtgagaa ctgggtgtcc gacgtcgcag aggtttctgc acgcactgtg | 960 |
| tgacaaaatt cttcattttt atttcaattc acttcacact ggttatgttt agggtggcat | 1020 |
| attacatttc aaagaaaaag cagttaggaa aaaaagttaa actgaaattt ctagctgaaa | 1080 |
| aagtaaaaaa aaaaaaaaaa gtaagttcat acagcaagaa tgtaaaccca ccacatccat | 1140 |
| caaacagcaa tcgagggagg ggacagagaa agcagtctga ggtacagagg tcaataacag | 1200 |
| tgctgtgatg atagtcagtc tatgcttata cttcctagag cagcaaaatc ataatgtagc | 1260 |
| caggtatggt agaatatctc tgaaatcttg gaataggaa ggcccctagc ttaaggccag | 1320 |
| cctgggctgc ttattagaat ttttgtctca gaagtcccac ccctgggggt taactctgtg | 1380 |
| atagaggact tgcctagagt gcacaaagtt ctgggtactg tcctcggtgc ctgaaaaata | 1440 |

-continued

```
aataattata atttagaatt aaatatatgc ccaacaattg cacagaaaca accttttttgg      1500 ggacagtaca ggtgacatcc agaaagcaaa ccaacaagca agcagtcaaa acatggggca      1560
gcgtagcttg acagcacccg tgtcacttta acttggtata ctacacttac ttgtgttttc      1620
ccgaccttgg gctaagctgt cacacatttt ttttaaaggct ttttaactct ttgtaaatca     1680
gaactgtctg tctctatgta acacttactg ggtgacatag acggggacag atgatatata     1740
tatatatata tatatatata tatatatatg tgtgtgtgtg tgtgtatata tatatatata     1800
tatatatata tatatatata tacatacata catatacata tacacacaca tatatgtatg     1860
tatgtatatg tgtgcatgta tatgtatatg tatatgtgta tgtgtatgtg tatgtgtgtg     1920
tgtgtgtgtg tgtgtgtgtg tgtgtgtgta tgtgtatgta tatatgtata tgtatatgta     1980
tatgtatatg tatatgtata tgtataatgt atatgtatat gtacatgaat gaaaggatgc     2040
aatcgcagtg atgtcattgg agctgaagta acccttcgct ttccaggtga tcaaatgcaa     2100
agctgcggtg ctatgggagc ttcacaaacc cttcaccatc gaggacatag aagtcgcacc     2160 cccccaaggcc catgaagttc gaattaaggt gactgcccct ttcaacttct gcaaagttag     2220
gttggaaaaa ctcgaaaagt actccatagc cacatccaga aatccgttaa tagccccttt     2280
catgtgctta attaatttgc tgctatcaat atcaaatgtc caaagtttga agtgactaga     2340
aagtatgttt aacctaatct cagaattttc tttagatgct tatgtgttta tgaagtgcta     2400
aaacatcttg agtccaaaac caactcatgt tgggtaatgt cttggtgcta atgtttgatt     2460
tctatttgca taaagcagca tgcattttca tatattccat aaaacacatt ttcagagcca     2520
cctactctac aggattgata attgagccat ttaattggga aaaggtaaac ggaaacactg     2580
gagaatcttg gagataaatg aactctttgg aatttggaag cagtaaggat tgttaggaag     2640
cccctcagaa gcacgactgc agacgaatag gcttgtgaaa cctccacaat cacaaacttg     2700
gttaactgga ctttaccttt aatccacaga tggtggccac tggtgtctgc cgctcagacg     2760
atcacgtggt tagtggaacc ctggtcacac ctcttcctgc agttttaggc catgagggag     2820
caggcattgt tgagagcgtt ggagaagggg tgacttgtgt gaaaccaggt acagaattca     2880
ccctcagggc ttgtgtttcg gttctgatct caagagcatc cctcccaaga gaggaagttg     2940
aggaagtggg agatgaaaag ccaggcaata gaaggcttcc tctgccccctt cctcccggca     3000 tgcctcagtc gtgctacatc caagcaagtc ttttctcttt caacatctgt ttatctccta     3060
catgtcaggc atcaagccag aggctcctat atgaagatct ggaagcacgg tgcccgtaag     3120
ggtgtgcagt ttataatctg ctaacttcta ctttattgtc cctgagcgct gtggactttc     3180
aaaacccaga cagaccttaa aaagtatccg aggcgggaaa tgcaggtcca ggttctgaga     3240
tacacggcag ctgttctgtg ctgaacgcag agacgtgaag gcttgcccta ctcgcaggac     3300
gcccaccata gttttaacca cacactggga caacatgatg gcttcctctt ttcctgtatg     3360
ctccttcttt atgaatatag ataaaataaa atgtaagagg gaatataagg gaaaatcata     3420
gccaaaggcc ttcaaaccca cagaccttct tatcattaat tgtggctgta ggtggtaggt     3480
cacacagtat ttattgcgtt acacatggct ccactttata tgttttttaag gtaaagggtg     3540 agcaaaacat aaaatttccg tgataccatc ccacattaat tttatctatg aaatataatg     3600 accaaaacctt ttttttttggt ccaataacat aggtagcata catgatttaa aaacaaaaat     3660
tatgttcatc ttcaaaaaga tcgctttagt caatagagtc agacttctct tctaaatgac     3720
taagctgtaa gcaaaaaata ggaaaagaac taatctggtt tgagttaagc ttgtattatt     3780
tcttttattc agaaaagaac aaaacaacaa caacaaacct agcagcaaaa tgacacccttt    3840
```

```
actcttcagg ttgcttcttc tatggcagaa aaatcaataa ttcataaata attatcttta   3900
aaaaacaaaa gtttcttgtt atttcccaga gaaagtattt aactcattaa gaactgagat   3960
ttccaaagca atttgtggct tgtcatgttt ttattatgct tcctcaaaaa ataactaaga   4020
tttttttaagc ctttatttca tagtaggaga agcacaatca ccttaaaaag ccaaaactgg   4080
accacgaaga aatgataacg tggctcaggg cataccatgc tcttatagag cacccaactg   4140
ggttactcac aaccacttgt aactccagct cctggggacc caacacccct tgctggcttc   4200
caagggcaca catacagaga tggcacacac acacaggtac tctcacatgc acacaaaaag   4260
aaaaaaacca acaccaacaa caaagtctta acaataaaaa gggcaaaagc taactatcaa   4320
gattcccact ttaatttgat ttcatgatca agtttaattt gttttatttt tactataaaa   4380
tattgcctgt atagtgtttc tttaatctta ctttttattga aactatcata tcagttctcg   4440
ccaaaatcta acaggaagat agcaactcat ttgcagagaa agtgtatatt tcttcttagc   4500
agcaagcata tccaaggttt gattaggata tgtacaaagc tcctaagaga aactgaggca   4560
cacaacaaag tttaactgct gacgggtgga aatggctggt ttcggctcat tttctctcc   4620
cgggaatctt caggcgcttt aaatgcgaat gactaattag actgacatag cctgggtgag   4680
gcctcatctc ctgagactt ttcaaagaca caatgtctct aataagcttc aagttgttgc   4740
tttattgatt tctggacaga catttaagtc attttgtttt tcttcatcca ggtgataaag   4800
tcattccact cttttcccct cagtgtggag aatgcaggat ttgcaagcac ccggaaagca   4860
acttttgtag ccgaagcgag tacgtttctt attgtcttct tgcacagttg ggtgggcaca   4920
ctgctttgtt ctgtctcatg tcctttgtat gcctgtgttt caccaaccag tctgctaatg   4980
cctcggggga ctttgcgcga aggcaccagc aggttctcct gcaagggaaa gcagatccac   5040
aactttatca gcaccagcac cttctcccag tacaccgtgg tagatgatat agcagtggcc   5100
aaaatcgatg gagcttcacc actggacaaa gtctgcctca tcggctgtgg gttctcaact   5160
ggctatggct ctgccgtcaa agtcgccaag gtaggatgga cagtgggcca tggaacaagc   5220
taagtgcata ttattggtac ctaaagggaa gacatggctc ctgggcgggc atcagagtat   5280
ttttgtagaa gtgaaataag cctctccagc cccagtgaga attcactcca cacacttgag   5340
agaagcaagg gaaagctcta taatagtgtg tgtctagttc tagctcttgc ccaaagagaa   5400
accagcgtct aacagaaatt atttgaagtt tgtttaggtc ttgggctgta acattctaca   5460
tatgccattg tctgcagatc tctgttatgt cccagctgca agactcactg agcaatgaaa   5520
tacattttaa ggagacagaa actggaaagc ttgactatat tggacaaatg ggagatttta   5580
taaagtggag atgccatcac tgttatttct aaagcaagcc acaatgggga tatttgtact   5640
gcagagatag tgccacaagt gtgcgttagt ttgttttaa gtagaccaac attgttacct   5700
agagccgtcc tgccttccag gtagaatttt ctagataaga aaaccaaggc ttttaatagc   5760
agagtagtac tccattgtgt agatgtacca catttctgt atctatccat tcctctgttg   5820
aaagacatct gggttctttc cagcttctgg ctattataaa taaggctgtt atgaacatag   5880
tggagcatgt gtccttgtta tatgttggag catcttctgt gtatatgccc aggagtatat   5940
gctgagtcct catgtcaaat ttctgaggaa ccaacagact gatttccaga gtggttgtaa   6000
tcctaccaac aatggaggaa tgtgcctctt tctccacatc ctcaccagca tctgctgaaa   6060
ttcttaggca aatggatgga actagaaaat atcatcctga atgaggtaac ccaatcacaa   6120
aagaacacac atagtatgca ttcactaata agtggggata ttagccgcaa agcatggaat   6180
actcaagata caattcacag atcacataaa gctcaagaag aaggagacct aagtgtgggt   6240
```

```
ccttcttaga aaggggaaca aaagactgtt ggaagccaat atagagatga agcataaagc    6300
agaggctgaa ggaaggtcat ccagagaatt cactccacac atgccccact tggggatcca    6360
tcccaaatac agtcaccaaa gccagacact attgtagatg ccaagaagtg catgctgaca    6420
ggagcatgat acagctgtct cctgagaggc cctgccagag ccttacaaat acagatgcag    6480
atgctcaaag ccaaccattg gactgagagc agggcccccaa atggaggatt tagagaaaga    6540
acttaaggag ccgaagggac taagacacca accaaagagt acacatggag ggacccatgg    6600
ctcagcctta tatgtaacag aggttggtct tgtcaggcat caatgggagg agaggttctt    6660
ggtcctgtga aggctcgata gatgcccag tgtaggagaa tgccagggtg gtgaggtggg    6720
agtgggtggg tgggtgaagg aacaccctca tagaagcagg gggaggggga gtagtataga    6780
gggtttctag aagtggggga aactggaaag ggggataata tttgaaatgt aaataaagga    6840
aatatccaat taaaaaatcc ttacatttaa aaaaagaaa gaaaaccaag gcttaatgat    6900
ggaccaggat ttaatggtac catgacccag tgcagcattg tgagctgcct gacagaggca    6960
tgctctttga taatgggaag agcctagtgg ccagctgtgg gctgtggttg tctctgtttg    7020
ttaacatatt catgatgtca gaggcatgcc ttttcctata gtttctgaca agcctgccta    7080
gtgtgttggt cttccttaac tcatgcaagc gacaacacca ggttagctaa actctacttt    7140
gtgtgatata atatttccta agcaagttca ttagtagatc cttcaagaca tcaatttatc    7200
actctaggat tctcctatgt cacttcatag atttatggtt ttgaattatt aatagaaaaa    7260
taaccccaga tggaactgga aaaaagaaa attcatcttt tttttaaaga tgaaaattat    7320
gctgattctg aattaagaaa aagtaaatat ttataaatat aataaatatt tataataaat    7380
ataatacatg tagaagatat tataatctgt gtattctata tgactaccaa aatttaaagc    7440
tgggaactct tgtagtagcc tattctccag ttgaaaagag atgtcactca tccatcatga    7500
tgggttccgc taggttctca agtagccaaa gcaaacggtt tgtcttctcc cagccttacc    7560
tgattcatct gcagcatggc cacccactga gtggatccca aagactcaa gagaacttaa    7620 gcaaagtatt gattacattt gagacctcat cactacatct tttcccttgc aaccaaaaca    7680
cacaaacaca cacacacaca aatacacata cgcatacaaa cacacatatg catacaaaca    7740
caaacagaaa catacacaca aacacactca taaccaacac acacacacac actagaagtt    7800
ttagatgttt agtttagac attttagatg gcgatttaa aaataatttc cttcccaaat    7860
ggttgaaaca aatccagtag ttatctttca ttttatgaaa actaaaatcc aggaagctaa    7920
agctaaaact attcatctaa atttccacta gggaaataaa gactagaatt cctctcaact    7980
tctctgctgc atctgaaact agagtgcaca ctggtcatga ctcccatcac agtaacaggc    8040
cttgcatttt tctgggccag gtggagagtg gcgatgtgtc ccagagcatt taagagcatt    8100
tgatggatga atgacaagat agacaccact aggggaagt gacagtcggg tatgggacac    8160
aggtggctgc accaattaaa tagacctaag ccagtcacag taatgaggag cctgcctttt    8220
ccaattctga ggctttagac ctaaatgcaa ttcgtgcttg tgctgttgtt taactgtctc    8280
agctggaagg ccgagtgtgc ctatttgcaa gccaagggta gttgtaatca tggattttaa    8340
ttaatcgtga ctaaaataca gattagcttt tgttgaagta tttgtcattt gcttcttcta    8400
aacattcagg cataaagtct cacagagatt acattggtct catgctatct tgtcttaaag    8460
tttcgtgtcc actttcctat tgctttaagc caggtatgac ttctacatgc ttctcagccg    8520
acttctgctc ccagtaccgt agttgtgact actgaaagtt agtgaaccaa gaaaggagtt    8580
cacgagcaaa gggcagttgg gttacctttt agtctcctgg agtaaccttg atcacttgtt    8640
```

```
tcatttattc aaattgctta tgtgcgtgtg taagatgtta ttgtaaagct ctcaaagatg    8700
taagtcgttt ttatttagaa ttcaaagatc atctggtaca gctgatctca acttgagttt    8760
tccccattga aataggaatg aggttccatt tgcagtgatt ccaatttaat tggtagaagc    8820
tgctatcaga ccttgagatt aacgaaagaa atccccagat atgtctaata catagcaaat    8880
cttgagtacc aatgatgtac actttgggca accataacca gaagtggatt tggcaacaaa    8940
tggaatgagg tagccgtgat aaaggacaca gcaaggcaat atgtgcagtg gggagcaccc    9000
cctaacagtc accattcaat ccacttttgt attttctgga aatacaggtg accccaggct    9060
ccacatgtgc cgtgtttggc ctcggaggtg tcggtctgtc tgtcatcatt ggctgtaaag    9120
cagcaggagc agccaggatc attgctgtgg acatcaacaa ggacaagttt gccaaggcca    9180
aagagttggg tgcaactgag tgcatcaacc ctcaagacta cagcaaaccc atccaggaag    9240
ttctccagga gatgaccgac ggaggggtgg acttttcgtt tgaagtcatc ggccgccttg    9300
acaccatggt atgtactttg gcacgccttg agatctgtcc ttccatctag aatgctctag    9360
gtagactaac agaaatctca tgcagaaagc tattttaga gtggtcatct tccatctcct    9420
gtttcctgct cagactgctt aattcgctgt tgagataaac ctttcatttt gtcagttctg    9480
caaacttgtc tcaagtgcta atcctccttt aatgcaacga agctttcaat ggggacactg    9540
tgaattaact tactgatttt ctgtaaaaaa tcacttcatc gagcaggttt aaatacaaag    9600
tctggtctta aatggatgaa tatgattttc tccctcattc ttaatatttt ttaatattta    9660
gaattgaata ttctgaaaag cattttaag tatcatcata cggccaaaag gaataatgaa    9720
caatttgggg cccaaggatc attttattaa cacacaacac gtagagggaa gtgactgatt    9780
tatacatcac catttagttc tcgttgcaga dacagcacag ggctgggcct tccaagcttc    9840
cagatctacc ggttgtagta aataccttt aaaaaagaa ttctggcata tctcctaaat    9900
ttaagagata cattttatag gattgcttat gatctccaca agacagtgca tataaaatac    9960
taactgtaga gccctgcca tgtggtaagc actcagtaaa ggtcagctga ggataatgat    10020
aagaaatact acggtcaagc ttagagcgat tggattttgg agtacaaatg acactacagt    10080
caagtagtta caaatgtcat cctttgctaa agaactgttc tccggttaca tctcacctaa    10140
ccaaagacct ctagaactct actgagaaat gtccccaggg agcaaggaag tcaccattat    10200
caaggctctc cacaaagtct tggcagagtt ggtgctggat aataggtatg gcgccctgag    10260
agtgatggtt tggtttagtt ttttttccat ccttgaactg tgacaagatg ccatagactg    10320
tagaagattc aagtgcacag cacctcctct ttccaaaccc aggcttccag ctctccccag    10380
agccactgct ctcgtggctc actggtagat ttctcaatct gctcatctta agctgggctg    10440
tcaattgact tgaagatcca aaagtctgat aaccacatgt tctgaggata tctggtttct    10500
aaacatcata ttgcaaaatc aaaggccact catgtatctt taaggattcc aaatgatttt    10560
ttactagaga atgtgtttta aacaaacaaa caaaaaacca aacaaactaa agaaaagtac    10620
ctattggaag gcaaaaactt cctggatgtc tacagctata gaataatata aactatcgc    10680 ataaccactt aaaacatgcc cattcttgat gtaagcaccc gaggagggac tcattaaatg    10740
agaatttgac aaatggttaa aagataagtt ttgatgatgt catcatttat cttcttcacc    10800
attagatttc tggctcagag tactagttta gaaattgtcc ttactgggca aatgaaaagt    10860
gaactaagca gttcatagag agttatgcga tggggaaaca atattctcct ttgagaacca    10920
gactttactt tctcatgatg attcttgcac ctttaaggaa gaattaaaca tagataagtt    10980
```

```
aattcattca ctctttcatt aaaaaaagaa aaaaatcttc agtgtacttc tttgtaatgc    11040
ctgaaactgc atagtgagga gagaccacaa aagactctac tttaactatt actctttatt    11100
ccagacttct gccctgctga gctgccatgc agcatgtggt gtaagcgtcg tcgtaggagt    11160
gcctcccaat gcccagaacc tctccatgaa ccccatgttg ctgctgctgg gacgcacctg    11220
gaagggagca atatttggcg gtatgtattc acagctcaag atcaatcctg catctgtctg    11280
tatacgtcag ggcgggcgtg tggatgtgtg tgtggaggac agagaacatt cgattcatta    11340
cctgggagcc atttgccacg ttctttgtga cagggtgtca cagtgaccag gctagccttg    11400
ctggctggaa tccactggtt cccttttatcc agagctggaa ttacaagaac tcccacaacc    11460
acatcagctg ttggttggtt ggttggttgg ttggttggtc agttgttgtt ttgttattca    11520
aactcaggtt tgactgagcc atctcctcag ctttgaggat caaatttttta atgtatttca    11580 gaatttcttc ccttctgtta cagagaaggt cagatttag aaggcaaaac aatttaaaaa    11640
catgaaaatt actgttctct ctaagcaaga actaatgcag gaaattgtaa gacaagcttc    11700
attgtgtccc cataaactag ccagggcttc ttctggctcc tcctacttcc taatgtcatt    11760
gtgagagccc caaaatgcct tataggacac aggaaatcca aggcagtagt agtccatgcc    11820
tataatcatg acctaagtct gaacagcggt gagaatggca aagctcccctt actttgagta    11880 caaacatctt caatatgatt tctctaggaa agaactaata agccaccttc attagcgaga    11940
gatcgcggtt tagaggggtg gcatacgata aaaatgttaa tgaaatgcag aatgtttttg    12000
agcctcagtg tctgtgcagc ctgcagacca ctgttctttt atgaacttta gtttccctgc    12060
aaagtctggt tggcttgctc cccccgccac tcccccacac attccctccc tccaaccccc    12120
caggctggat ctcatggaga tgttgctctc cttccagggt ttaagagtaa agattctgtc    12180
cctaaacttg tggctgactt catggctaag aagtttccgt tggacccgtt aattacccat    12240
gttttacctt tcgagaaaat aaatgaagca tttgacctgc ttcgttctgg aaagaggtaa    12300
gctttgagat tattttttatg gcagaggaat tggctaacag aaaatgaagg agaagtggga    12360
taagaccata aatgaagggg gtgggggaag gggctggctt ctgtcaccag tttggctctg    12420
cacacaggta tatgacatag gacaattgca aacctaagct ttagtttcca cagttcctaa    12480
aggtgacaat atgtgataat ccaccttgta gtattgctgt ttaggatgag gtttaaatga    12540
gataaccatg ccttaaaagc ttccataaag cacatggcag gtagcaagga ggaaatggct    12600
ggtgttgccc attgttacac aagggatcca gacttttagt gttgtttaag agtgctaaac    12660
tagaaccgga atcaaaatgg cagtcacatc aggatgttaa gtgtgagttt agagctggag    12720
agaatgcaag agcgatcaga aaggtggatt gctcgtttac tgacttgacc ttgggcatag    12780
catggttggg aacccggata gatttctca gagactccta acatgtcttc tactcacttt    12840
tatggtgagt tatggaatgt gaaatcacta tcttctgttc tgtatttcag catccgtacc    12900
gtcctgactt tctgagatca tgtggatgcc ttcccacgca ccagtttctg aaccctaaac    12960
cagactgatt caagcaccag ccacatcaca gccttaatct ttgctctttta gagacacagc    13020 caataaagta cttgtgtaag ctctcca                                        13047
```

<210> SEQ ID NO 29
<211> LENGTH: 2024
<212> TYPE: DNA
<213> ORGANISM: Arabidopsis thaliana

<400> SEQUENCE: 29

```
tctacttctt ccaattacca gctgctatat aaatcccctt ctctgtttct cttttcttac    60
atcacaatca cacaaaacta acaaaagatc aaaagcaagt tcttcactgt tgataatgtc   120
taccaccgga cagattattc gatgcaaagg ttttctttt attctgtctt tttccaaata   180
tttattgatc ggttacattt ctgttgaggt ttttgttatg aatccacaat ttctatgttg   240
aattaacaaa acctgtgtcg tttttttgtg gtggttgcag ctgctgtggc atgggaagcc   300
ggaaagccac tggtgatcga ggaagtggag gttgctccac cgcagaaaca cgaagttcgt   360
atcaagattc tcttcacttc tctctgtcac accgatgttt acttctggga agctaaggta   420
gagtaatcaa tttattacac tccaaattca taatcaagtt ctaattttt tagaattcta   480
attttttatc taaaaaaatt caacctttt gattccacag ggacaaacac cgttgtttcc   540
acgtatcttc ggccatgaag ctggagggta atagaaacac taatcttctt tgcttcgttt   600
tggatatttt taaggtttta gagattcaag gtcgtttttt ttgttgttgt gtaggattgt   660
tgagagtgtt ggagaaggag tgactgatct tcagccagga gatcatgtgt tgccgatctt   720
taccggagaa tgtggggagt gtcgtcattg ccactcggag gaatcaaaca tgtgtgatct   780
tctcaggatc aacaccgagc gaggagggat gattcacgat ggtgaatcaa gattctccat   840
taatggcaaa ccaatttacc atttccttgg gacttccacg ttcagtgagt acacagtggt   900
tcactctggt caggttgcta agatcaatcc ggatgctcct cttgacaagg tctgtattgt   960
cagttgtggt ttgtctactg ggttaggagc aactttgaat gtggctaaac ccaagaaagg  1020
tcaaagtgtt gccatttttg gtcttggtgc tgttggttta ggcgctgcag aaggtgctag  1080
aatcgctggt gcttctagga tcatcggtgt tgattttaac tctaaaagat tcgaccaagg  1140
tattcaaaaa gatgatagtc tgttttgac tatgttcttc tataatctcc cttcacttac  1200
attgaatttg atatgttatt ggcagctaag gaattcggtg tgaccgagtg tgtgaacccg  1260
aaagaccatg acaagccaat tcaacaggtg atcgctgaga tgacggatgg tggggtggac  1320
aggagtgtgg aatgcaccgg aagcgttcag gccatgattc aagcatttga atgtgtccac  1380
gatgtaatcc tcccttcaca tcattcggac caaaactttt gtaactacat tgtgggtatc  1440
tgaacttatc acatatgatg ttgtttcagg gctggggtgt tgcagtgctg gtgggtgtgc  1500
caagcaaaga cgatgccttc aagactcatc cgatgaattt cttgaatgag aggactctta  1560
agggtacttt cttcgggaac tacaaaccca aaactgacat tcccgggggtt gtggaaaagt  1620
acatgaacaa ggtaatgaga agctttgata tcttatgatg ccaactttga atatatatca  1680
atgttctgat gattttatg acataggagc tggagcttga gaaattcatc actcacacag  1740
tgccattctc ggaaatcaac aaggcctttg attacatgct gaagggagag agtattcgtt  1800
gcatcatcac catgggtgct tgaagccatt ctctcgcaga tgatgttcac tttgtgtttt  1860
acttcccttta tgcattcaca gcaataaaag aaagaaatct ccatcgcttt tggttttctt  1920
ctctgtctta agttagtcgt tttcgtgtct aatctattac ttatcattgt aatagactct  1980
tcttctattg agatttgaat ataaactaaa acacattcca tttt                  2024
```

<210> SEQ ID NO 30
<211> LENGTH: 2655
<212> TYPE: DNA
<213> ORGANISM: Saccharomyces cerevisiae

<400> SEQUENCE: 30

```
atggatccta atagtaacag ttctagcgaa acattacgcc aagagaaaca gggtttccta    60
gacaaagctc ttcagagggt gaagggcata gcactgcgac gaaacaatag taacaaagat   120
catacaacag atgatacgac aggtagcata cgaaccccta cgagcttgca gcggcaaaat   180
tctgacaggc aatctaatat gacatccgtg tttacggatg acatttctac catagacgac   240
aactcaattt tattttcaga gcctcctcag aaacaatcta tgatgatgtc tatatgcgta   300
ggtgttttg ttgcagttgg cggattttta tttggttatg atacaggtct gatcaacagt    360
attacatcta tgaactatgt gaagtcacac gtagcaccta atcacgattc atttaccgcc   420
caacaaatgt ccattttggt gtcattttg tcattgggaa cttttttgg ggctttaact     480
gcaccattta tatctgattc gtatggcagg aagcctacta tcattttcag tacaattttc   540
atcttctcta tcggaaattc tttacaggta ggtgctggag aatcacatt attgattgtg    600
ggaagggtca tttcaggtat cggtataggc gcaatttcag cggttgttcc attataccaa   660
gcagaagcta cacataaatc attaagaggt gctattattt ctacttacca atgggccatt   720
acctggggct tgctcgtgtc aagtgcagtg tcgcaaggga cacacgcaag aaacgacgca   780
tcttcgtatc ggattcccat agggttgcaa atatgtctggt cgtcatttct cgctatcggg   840
atgttcttc tccctgagag tccacgctat tacgttttga agacaagct agatgaagca     900
gctaaatctt tatcgttttt aagaggtgta ccagtccatg attctgggtt actggaagaa   960
ctagttgaaa taaaggcaac atatgattac gaggcatctt ttggttcttc gaacttcatt  1020
gattgtttta tttcaagtaa aagtagacca agcaaactc taaggatgtt tacgggaatt   1080
gcccttcaag catttcaaca attttcaggt atcaacttta tattttacta cggtgtcaat  1140
ttcttcaata agacaggagt cagtaatagt tatctggttt catttataac ctatgctgtt  1200
aatgttgtct ttaatgttcc tggtttgttt tttgtggaat tttttggtag acgtaaggtg   1260
ctggttgttg ggggtgttat catgactata gccaactta ttgtggccat tgttgggtgt    1320
tccttaaaga ctgtagcggc cgcaaaagtt atgatagcat ttatatgtct attcatagct   1380
gccttttctg ctacatgggg tggtgttgtt tgggttattt cagcagaact gtacccattg   1440
ggtgtgagat ctaaatgtac ggctatatgc gctgctgcta actggcttgt aaactttatt   1500
tgtgctttaa ttccccctta tattgtagat actgggtcgc atacatcatc attaggtgca   1560
aaaatattct tcatttgggg ctccttaaat gcgatggggg tgatagttgt ttacttgacc   1620
gtttatgaaa cgaagggttt gacattgaaa gagattgatg aattatatat taagtcatcc   1680
actggtgtcg tgtcaccaaa atttaataaa gatattaggg aacgcgcact taaattccaa   1740
tacgatcctt tgcaaagatt agaagacgga agaacactt tgttgctaa aagaaataat     1800
tttgacgatg aaacaccaag aaatgatttt cgaaatacga tatcgggcga aatagatcat   1860
agtcccaatc aaaagaagt tcattctatc ccagaacgtg ttgatattcc tactagtaca    1920
gaaattcttg aaagcccgaa caaaagtagt ggtatgacag tccctgtgtc accttctctg   1980
caagacgttc caatcccgca acaacagag cctgctgaaa ttcgaaccaa atatgtggac    2040
ctaggaaatg gcttggtct taatacgtat aatagagggc ctccctcact ctcaagcgac    2100
tcaagcgaag attacacaga agatgaaata ggcgggccct catctcaagg cgaccaaagt   2160
aatagaagta ctatgaatga tattaatgat tatatggcac gtctcattca cagtacttct   2220
actgcaagta acacgacaga taagttctcc ggtaaccaaa gtacccttcg ttaccacacg   2280
gcttcctcac attcggatac aactgaagag gacagcaatt tgatggacct gggaaacggg   2340
```

```
cttgccttga atgcttataa cagaggtcca ccttcaattt taatgaattc cagtgatgaa   2400
gaggcaaatg gtggtgagac gtctgataat ttgaacacag ctcaagactt ggctggtatg   2460
aaggaacgaa tggcgcagtt tgcgcagagc tatattgaca agagaggcgg tctggaacct   2520
gaaactcaat ctaatatttt gagcacttct ctctccgtga tggctgacac taatgaacat   2580
aataatgaaa tcctccactc aagcgaagaa acgccacta  atcaacctgt aaatgaaaat   2640
aatgatttga aataa                                                    2655
```

<210> SEQ ID NO 31
<211> LENGTH: 2655
<212> TYPE: DNA
<213> ORGANISM: Saccharomyces cerevisiae

<400> SEQUENCE: 31

```
atggatccta atagtaacag ttctagcgaa acattacgcc aagagaaaca gggtttccta     60
gacaaagctc ttcagagggt gaagggcata gcactgcgac gaaacaatag taacaaagat    120
catacaacag atgatacgac aggtagcata cgaaccccta cgagcttgca gcggcaaaat    180
tctgacaggc aatctaatat gacatccgtg tttacggatg acatttctac catagacgac    240
aactcaattt tattttcaga gcctcctcag aaacaatcta tgatgatgtc tatatgcgta    300
ggtgtttttg ttgcagttgg cggatttta  tttggttatg atacaggtct gatcaacagt    360
attacatcta tgaactatgt gaagtcacac gtagcaccta atcacgattc atttaccgcc    420
caacaaatgt ccattttggt gtcatttttg tcattgggaa ctttttttgg ggctttaact    480
gcaccattta tatctgattc gtatggcagg aagcctacta tcattttcag tacaatttc    540 atcttctcta tcggaaattc tttacaggta ggtgctggag aatcacatt  attgattgtg    600 ggaagggtca tttcaggtat cggtataggc gcaatttcag cggttgttcc attataccaa    660
gcagaagcta cacataaatc attaagaggt gctattattt ctacttacca atgggccatt    720
acctggggct gctcgtgtc  aagtgcagtg tcgcaaggga cacacgcaag aaacgacgca    780
tcttcgtatc ggattcccat agggttgcaa tatgtctggt cgtcatttct cgctatcggg    840
atgttctttc tccctgagag tccacgctat acgttttga  aagacaagct agatgaagca    900
gctaaatctt tatcgttttt aagaggtgta ccagtccatg attctgggtt actggaagaa    960
ctagttgaaa taaaggcaac atatgattac gaggcatctt ttggttcttc gaacttcatt   1020
gattgtttta tttcaagtaa aagtagacca aagcaaactc taaggatgtt tacgggaatt   1080
gcccttcaag catttcaaca attttcaggt atcaacttta tattttacta cggtgtcaat   1140
ttcttcaata agacaggagt cagtaatagt tatctggttt catttataac ctatgctgtt   1200
aatgttgtct ttaatgttcc tggttttgttt tttgtggaat ttttttggtag acgtaaggtg   1260 ctggttgttg ggggtgttat catgactata gccaacttta ttgtggccat gtttgggtgt   1320
tccttaaaga ctgtagcggc cgcaaaagtt atgatagcat ttatatgtct attcatagct   1380
gccttttctg ctacatgggg tggtgttgtt tgggttattt cagcagaact gtacccattg   1440
ggtgtgagat ctaaatgtac ggctatatgc gctgctgcta actggcttgt aaactttatt   1500
tgtgctttaa ttacccctta tattgtagat actgggtcgc atacatcatc attaggtgca   1560
aaaatattct tcatttgggg ctccttaaat gcgatggggg tgatagttgt ttacttgacc   1620
gtttatgaaa cgaagggttt gacattagaa gagattgatg aattatatat taagtcatcc   1680
actggtgtcg tgtcaccaaa atttaataaa gatattaggg aacgcgcact taaattccaa   1740
tacgatcctt tgcaaagatt agaagacgga aagaacactt tgttgctaa  aagaaataat   1800
```

| | |
|---|---:|
| tttgacgatg aaacaccaag aaatgatttt cgaaatacga tatcgggcga aatagatcat | 1860 |
| agtcccaatc aaaagaagt tcattctatc ccagaacgtg ttgatattcc tactagtaca | 1920 |
| gaaattcttg aaagcccgaa caaaagtagt ggtatgacag tccctgtgtc accttctctg | 1980 |
| caagacgttc caatcccgca acaacagag cctgctgaaa ttcgaaccaa atatgtggac | 2040 |
| ctaggaaatg ggcttggtct taatacgtat aatagagggc ctccctcact ctcaagcgac | 2100 |
| tcaagcgaag attacacaga agatgaaata ggcgggccct catctcaagg cgaccaaagt | 2160 |
| aatagaagta ctatgaatga tattaatgat tatatggcac gtctcattca cagtacttct | 2220 |
| actgcaagta acacgacaga taagttctcc ggtaaccaaa gtaccctccg ttaccacacg | 2280 |
| gcttcctcac attcggatac aactgaagag acagcaatt tgatggacct gggaaacggg | 2340 |
| cttgccttga tgcttataa cagaggtcca ccttcaattt taatgaattc cagtgatgaa | 2400 |
| gaggcaaatg gtggtgagac gtctgataat ttgaacacag ctcaagactt ggctggtatg | 2460 |
| aaggaacgaa tggcgcagtt tgcgcagagc tatattgaca agagaggcgg tctggaacct | 2520 |
| gaaactcaat ctaatatttt gagcacttct ctctccgtga tggctgacac taatgaacat | 2580 |
| aataatgaaa tcctccactc aagcgaagaa aacgccacta atcaacctgt aaatgaaaat | 2640 |
| aatgatttga aataa | 2655 |

```
<210> SEQ ID NO 32
<211> LENGTH: 1581
<212> TYPE: DNA
<213> ORGANISM: Candida albicans

<400> SEQUENCE: 32
```

| | |
|---|---:|
| atgagtgcaa atatccaagc tcttatgaaa agctatgtca attttgacga acacacttct | 60 |
| ggttccgctg ccagaggtat tttaatcggt atgtttgctg cttttggtgg gttttttgttt | 120 |
| ggttacgaca ctggtactat ttctggtgta ttgtctatgg actacgttaa agccagattc | 180 |
| cccaacaaca aaaccgattt cacttctggt gaaagttccc ttattgtctc cattttatca | 240 |
| gtcggtactt tgttggttc cttgattgcc ccattgtttt ccgatagaat tggtcgtaga | 300 |
| tggacattga ttttatctac tttgattgtt tttaacttgg gagttctttt acaaactgtt | 360 |
| gccactgaaa agaaattgct tattgcaggt agagccattg ccggtactgg tgttggttta | 420 |
| atttcatctg ttattcctaa ttatatttcg gaaacaacac caaagtgggc tagaggtgct | 480 |
| gtcactgctt cataccaatg gatgatcacc tggggtcttt taattgctgc ttgtgccaac | 540 |
| aagggttccc aaggtagaaa agactctggt tcctatagaa tacccattgg tattcaatt | 600 |
| ttgtgggcat tgattttggg tattggtttc ttgtttctcc cagaaacccc aagatactgg | 660 |
| gtttccaagt ctgaagaaac taaagctaaa gattctttga aagaattag aaacttgcct | 720 |
| gttgatcacc cagatttggt gctggaatac gatgacatta agcaaacttt tgatttcgaa | 780 |
| tccaaatatg ccacttcttc ttggacccaa gttttcaaaa acgttaacaa caacaccac | 840 |
| agattattca ctgggggttgc catccaagct ttgcaacaac ttactggtat taatttcatc | 900 |
| ttctactatg gtactcaatt cttcaagcgt tctggtattg aagatccttt ccttatccaa | 960 |
| cttgccacta atattgttaa tgttggtatg actgtgccgg tattattttt ggttgaaacc | 1020 |
| tgggggtagaa gaccattgtt gatggccggt agtgttgtta tggctgtctc ccaattgatt | 1080 |
| gttgccattg ttggtgttgc tgctagcagt catgctgcaa atcaatgttt agttgctttc | 1140 |
| agttgtatttt tcattgctgg tttcgcagca acttggggac ctcttgttg ggctatttgt | 1200 |
| ggtgaatcct tgctttgaa cgtgagactg aaatcaatct cctgtgtac cgcaagtaac | 1260 |

```
tggctttgga atttcggtat tggttatgct actccttata tggttgattc aggtaaaggg     1320
aacgccgact tgggttcaaa ggtgtttttc atttggggtg gatgtaacgt cattggtggg     1380
ttgtttgcat actttatggt ttacgaaacc aagagtctta cattagaaca agttgatgaa     1440
ttgtacttga agttgatca cgcttggcaa tctaaaggat tgttcctag tgtccacgca       1500 tttagagatg atggcgatat tgagcacatc tcttctgatg aaaagccga aatggttgaa      1560 gttgatgaaa attccgttta a                                                1581
```

<210> SEQ ID NO 33
<211> LENGTH: 111
<212> TYPE: DNA
<213> ORGANISM: Ostreococcus tauri

<400> SEQUENCE: 33

```
cgcgcgtcgt gcgagtggct cgatcgatct cacgctcgat cgcgtctgag aacacatcgc     60
tggaacttga ctcaggataa tacctgcgta aggaacgacc gcggcatcgc g              111
```

<210> SEQ ID NO 34
<211> LENGTH: 1362
<212> TYPE: DNA
<213> ORGANISM: Artificial sequence
<220> FEATURE:
<223> OTHER INFORMATION: Synthetic construct

<400> SEQUENCE: 34

```
tggctgcgtc tggtgggacc gttgtatacg ccggtagtgg tttgcggggc tacggcgagt     60
tggtcatcat caaacacaac gagacctacg tgagtgccta cggtcacaac cgcaggctgc    120
tggtgcggga agggcaacag gtcaaggtag ggcaatcgat tgccgagatg ggctccacag    180
gaaccgatcg ggtgaagctg cacttcgaga ttcgccgcca gggtaagcct gtcgatccac    240
tgcaatattt gccacgtcgc tgaccgggag ttcgcccgcc cacatcatgt aggtgagcgg    300
gtccgggcgt gtccagcggg aaaggaatcg cccgggcttg agtcgaactc atgcaaggga    360
taacgacatg gcactcaaaa agaagggcc ggagtttgac cacgatgatg aagtgctcct     420
cctggagccc ggcatcatgc tggacgagtc gtctgccgac gagcagcctt ctccccgggc    480
aactccaaaa gccaccactt ccttctcttc caaacaacac aagcacatcg actacacgcg    540
cgcgttggac gcaacgcagc tgtatctcaa cgaaatcggt ttctcgcccc tgttgacgcc    600
cgaagaggaa gtccacttcg ctcgtctggc gcagaagggc gatcccgctg tcggaagcg    660 gatgatcgag agcaacctgc ggttggtggt gaagatcgcc cggcgctatg tcaatcgcgg    720
actgtccctg ctcgacctga tcgaggaagg caacctaggc ctgatccgcg ccgtggagaa    780
gttcgatccg gagcgcggat tccggttctc gacctacgcc acctggtgga tccgccagac    840
catcgagcgg gccatcatga accagacccg gaccattcgc ttgccgatcc atgtggtcaa    900
ggagctcaac gtctacctgc gtgcggcgcg ggaactgacc cacaagctcg accacgaacc    960
ttcacccgaa gaaatcgcca acctgctgga gaagccggtc gccgaggtca gcgcatgct    1020 cggcctgaac gaacgggtga cttcggtaga cgtctctctt ggtccggact cggacaagac    1080
cctgctggat acgctcaccg acgatcgccc caccgatccg tgcgagctgc tgcaggatga    1140
cgatctcagc gaaagcagct gacggaactc accgacaagc agcgtgaggt ggtgattcgc    1200
cgcttcggct tgcgcggtca cgaaagcagc acgctggaag aggtcggcca ggaaatcggc    1260
ctgacccgcg agcgggttcg tcagatccag gtcgaggcgc tgaagcgcct gcgggagatt    1320
ctggagaaga atggcctgtc gagtgacgcg ctgttccagt ga                       1362
```

```
<210> SEQ ID NO 35
<211> LENGTH: 18
<212> TYPE: DNA
<213> ORGANISM: Artificial sequence
<220> FEATURE:
<223> OTHER INFORMATION: Synthetic construct

<400> SEQUENCE: 35
cccgccgcca ccatggag                                                 18

<210> SEQ ID NO 36
<211> LENGTH: 13
<212> TYPE: DNA
<213> ORGANISM: Artificial sequence
<220> FEATURE:
<223> OTHER INFORMATION: Synthetic construct

<400> SEQUENCE: 36
tcacacagga aag                                                      13
```

GLUCOSE SENSORS AND METHODS OF USE THEREOF

CROSS REFERENCE TO RELATED APPLICATIONS

This application is a continuation application of U.S. application Ser. No. 15/498,630, filed on Apr. 27, 2017, which is a continuation application of U.S. application Ser. No. 14/112,984, filed on Jun. 9, 2014, which is a U.S. national phase application under 35 USC 371 of international application number PCT/US2012/034170, filed Apr. 19, 2012, which claims priority to U.S. provisional application Ser. No. 61/478,274, filed Apr. 22, 2011, which are hereby incorporated herein by reference in their entirety for all purposes.

CROSS REFERENCE TO SEQUENCE LISTING

The DNA and RNA described herein are referred to by a sequence identifier number (SEQ ID NO). The SEQ ID NO corresponds numerically to the sequence identifiers <400>1, <400>2, etc. The Sequence Listing, in written computer readable format (CFR), is incorporated by reference in its entirety.

BACKGROUND

Diabetes is a degenerative disease, which is caused by abnormal levels of glucose in the cell. These abnormal levels of glucose are not easily predictable and or measurable. Currently, home use technologies to determine different levels of glucose are not very accurate or are not able to determine lower levels (below 20 mg/dl). Additionally, the abnormal levels of glucose have been correlated with the production of insulin. Type 1 diabetes is where the body is unable to produce insulin. Type 2 diabetes is when insulin is produced but the body destroys the insulin or is unable to recognize it.

Currently, the most used technologies to determine glucose levels involve enzyme reaction methods. These methods determine glucose in whole blood, plasma or serum. The methods include glucose oxidase, hexoquinase, and glucose dehydrogenase enzyme methods. The products of these reactions between the enzyme and blood sugar can be determined with colorimetric and spectrophotometric assays. Alternatively, they can be measured by the electric current produced in the reaction, which is the case for most commercially-available glucose meters. These methods are accurate and are becoming more sensitive, detecting glucose concentrations from 0 to 500 mg/dl for laboratory assays and 20 to 500 mg/dl for home monitoring. However, these methods can give falsely high values of glucose with different environmental or medical treatments. These methods can also provide uncertain values such as the incompatibility of the meters and the strips, which is one of the persistent problems of the methods.

The cost of current methods for measuring blood sugar levels is also an impediment, which ranges from about $0.35 to $1.00 for each strip used in home monitoring methods. Type 1 diabetics may test as often as 4 to 10 times a day. Thus, daily testing can be expensive. Manufacturers often provide meters at no cost to induce the use of the profitable test strips. For clinical laboratories, glucose determinations range from $3 to over $100 in the US and around the world. In the case of insulin analysis, prices range from $25 to $130 USD in the US and around the world. Diabetes diagnostic tests that include specific tests for measuring glucose and insulin levels can cost between $190 to $350, which is very expensive for diabetic patients.

The sensors and methods described herein address the issues of sensitivity and cost that are problems associated with current technologies available on the market.

SUMMARY

Described herein are glucose and insulin sensors. The sensors are composed of host cells such with DNA specifically designed to produce fluorescence when the cells come into contact with glucose and/or insulin in the sample. Once the fluorescence has been quantified, it can be correlated with the amount of glucose and/or insulin present in the sample. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
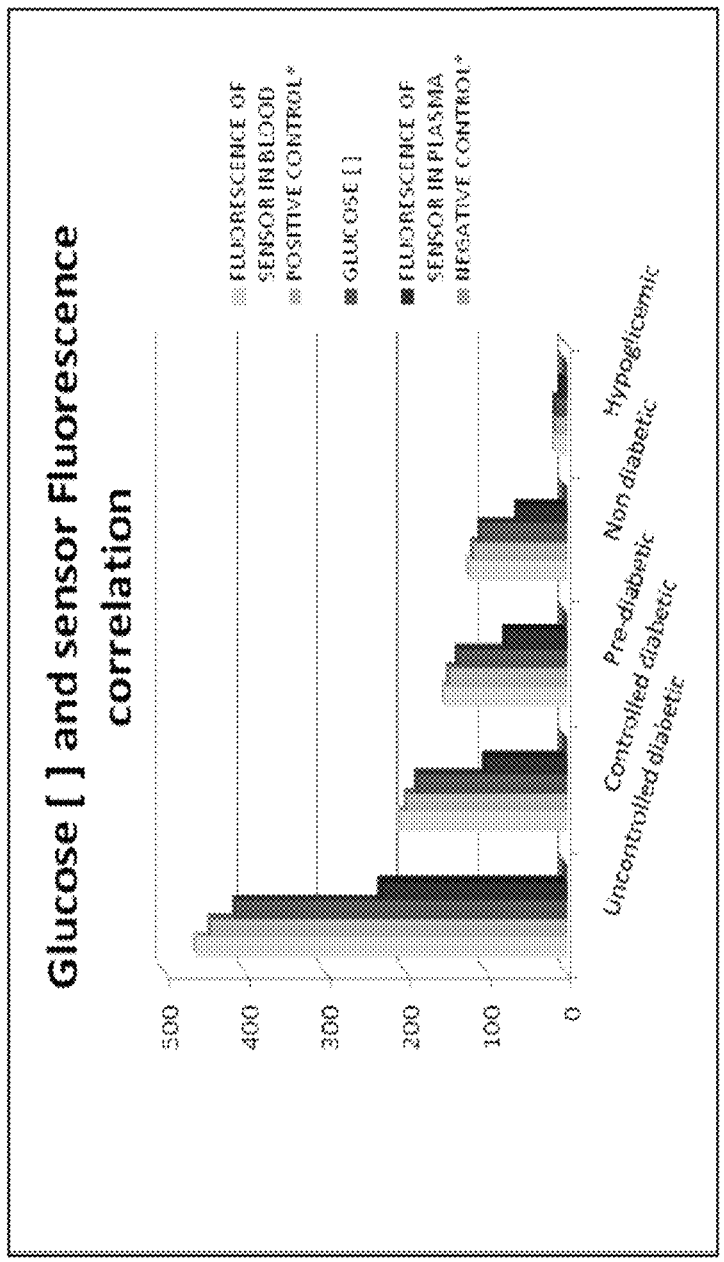
FIG. 1 shows (A) the equivalent proportion correlation of sensor fluorescence with clinical glucose values, demonstrating a direct relation for different patients including uncontrolled diabetic, controlled diabetic, pre-diabetic, non-diabetic and hypoglycemic patients; and (B) the equivalent proportion correlation of the DNA sensor and fluorescence when testing for glucose in different patients including uncontrolled diabetic, controlled diabetic, pre-diabetic, non diabetic and hypoglycemic patients.
Figure 1:
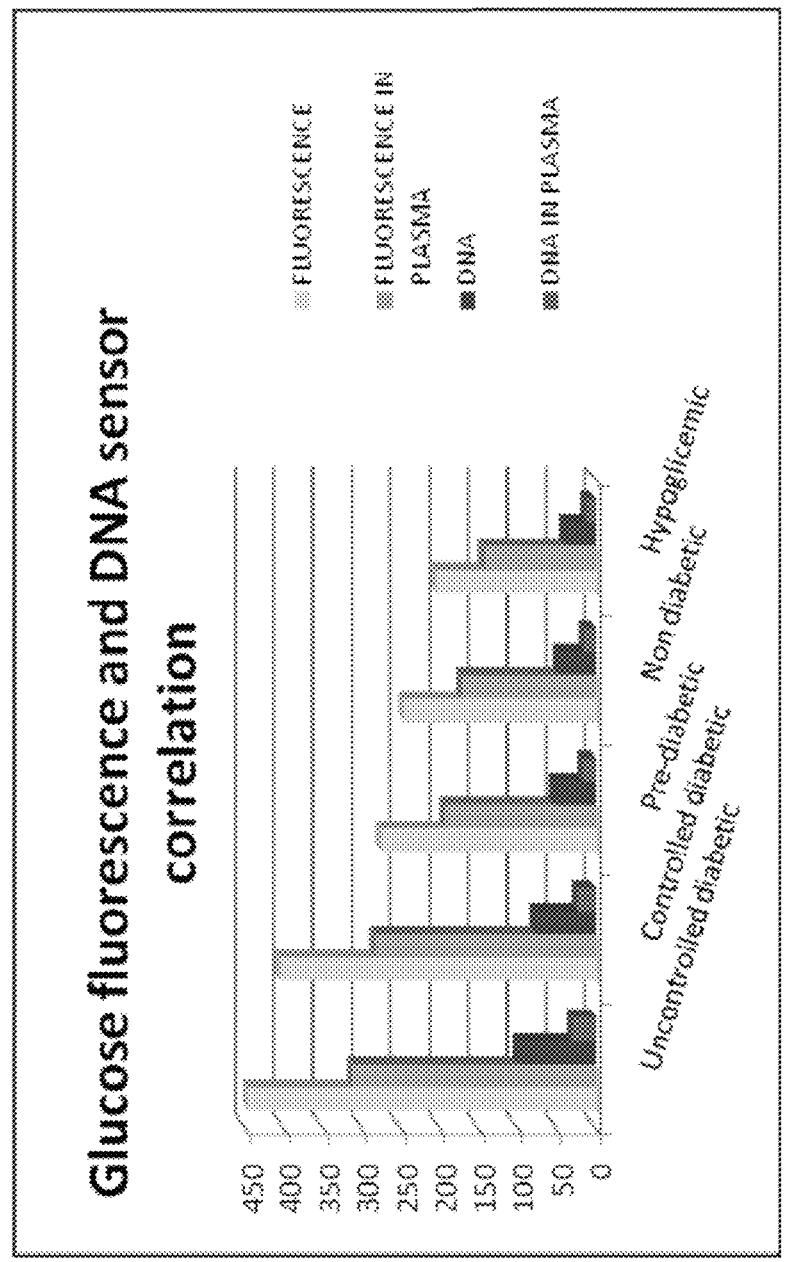

Before the present compounds, compositions, articles, devices, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a bioactive agent" includes mixtures of two or more such agents, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or can not be substituted and that the description includes both unsubstituted lower alkyl and lower alkyl where there is substitution.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Described herein are glucose and insulin sensors. The sensors are composed of host cells incorporated with DNA specifically designed to produce fluorescence when the cells come into contact with glucose and/or insulin in the sample. In one aspect, the sensor comprises a host cell comprising (1) a first DNA, wherein the first DNA comprises the following components in the following sequence: a glucose promoter, a glucose protein receptor, a ribosomal binding site, terminator, and a first reporter protein; (2) a second DNA, wherein the second DNA comprises the following components in the following sequence: an insulin promoter, a human insulin protein, a ribosomal binding site, a terminator, and a second reporter protein, or a combination thereof. In this aspect, the first DNA (referred to herein as "the glucose DNA") is specific to glucose, and the second DNA (referred to herein as "the insulin DNA") is specific to insulin. As will be discussed in detail below, the host cell can be transformed with both the glucose and insulin DNA in order to quantify the amount of glucose and insulin in the sample.

The host cells as referred to herein include their progeny, which is any and all subsequent generations formed by cell division. It is understood that all progeny may not be identical due to deliberate or inadvertent mutations. A host cell may be "transfected" or "transformed," which refers to a process by which exogenous nucleic acid is transferred or introduced into the host cell. A transformed cell includes the primary subject cell and its progeny. The host cells can be naturally occurring cells or "recombinant" cells. Recombinant cells are distinguishable from naturally occurring cells in that they do not contain a recombinantly introduced nucleic acid. In one aspect, the host cell is a prokaryotic cell, such as, for example, *E. coli*. In other aspects, the host cell is yeast.

In order to effect expression of the glucose and insulin DNA, the DNA must be delivered into the host cell. This delivery may be accomplished in vitro, as in laboratory procedures for transforming cells lines using well developed procedures. Transformation of bacterial cell lines can be achieved using a variety of techniques. One method includes using calcium chloride. The exposure to the calcium ions renders the cells able to take up the DNA, or competent. Another method is electroporation. In this technique, a high-voltage electric field is applied briefly to cells, apparently producing transient holes in the cell membrane through which plasmid DNA enters. Exemplary procedures for transforming yeast with the glucose and insulin DNA are provided in the Examples. The glucose DNA and insulin DNA can be independently incorporated into the host cells (i.e., separate cell lines containing just glucose DNA and insulin DNA). Alternatively, the glucose DNA and insulin DNA can be incorporated into the same cells.

Once the glucose and/or insulin DNA has been incorporated into the host cell, the cells are cultured such that the cells multiply. A satisfactory microbiological culture contains available sources of hydrogen donors and acceptors, carbon, nitrogen, sulfur, phosphorus, inorganic salts, and, in certain cases, vitamins or other growth promoting substances. The addition of peptone provides a readily available source of nitrogen and carbon. Furthermore, different media results in different growth rates and different stationary phase densities. A rich media results in a short doubling time and higher cell density at a stationary phase. Minimal media results in slow growth and low final cell densities. Efficient agitation and aeration increases final cell densities. A skilled artisan will be able to determine which type of media is best suited to culture a specific type of microorganism.

The glucose and insulin DNA referred to herein can be part of a vector that is incorporated into the host cells. In general, plasmid vectors containing replicon and control sequences that are derived from species compatible with the host cell are used in connection with these hosts. The vector ordinarily carries a replication site, as well as marking sequences that are capable of providing phenotypic selection in transformed cells. Plasmid vectors are well known and are commercially available. Such vectors include, but are not limited to, pWLNEO, pSV2CAT, pOG44, PXT1, pSG (Stratagene) pSVK3, pBSK, pBR322, pYES, PBSKII, and pUC vectors.

It is understood that one way to define the variants and derivatives of the glucose and insulin DNA herein is through defining the variants and derivatives in terms of homology/identity to specific known sequences. Those of skill in the art readily understand how to determine the homology of two nucleic acids. For example, the homology can be calculated after aligning the two sequences so that the homology is at its highest level. Another way of calculating homology can be performed by published algorithms (see Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989, which are herein incorporated by reference for at least material related to nucleic acid alignment).

It is understood that the description of conservative mutations and homology can be combined together in any combination, such as embodiments that have at least 70%, 75%, 80%, 85%, 90%, 95%, or 99% homology to a particular sequence wherein the variants are conservative mutations. It is understood that any of the sequences described herein can be a variant or derivative having the homology values listed above.

The glucose DNA comprises the following components in the following sequence: a glucose promoter, a glucose protein receptor, a ribosomal binding site, terminator, and a first reporter protein. In certain aspects, the glucose DNA further comprises a ribosomal switch between the glucose protein receptor and the ribosomal binding site that can enhance translation and protein expression.

In one aspect, the glucose promoter in the glucose DNA is an ADH1 glucose promoter having SEQ ID NO. 1 or a derivative or variant thereof. In another aspect, the glucose promoter is SEQ ID NOS. 30-32 or a derivative or variant thereof.

In another aspect, the glucose protein receptor in the glucose DNA comprises a snf3 glucose protein receptor having SEQ ID NO. 2 or a derivative or variant thereof. In another aspect, the glucose protein receptor is SEQ ID NOS. 20-29 or a derivative or variant thereof.

In a further aspect, the ribosomal binding site in the glucose DNA comprises SEQ ID NOS. 4, 35, 36, or a derivative or variant thereof.

In another aspect, the terminator in the glucose DNA comprises SEQ ID NO. 5 or a derivative or variant thereof.

In certain aspects, when the glucose DNA further includes a ribosomal switch, the switch comprises SEQ ID NOS. 4, 34, 35, or a derivative or variant thereof.

In another aspect, the glucose DNA comprises the following components in the following sequence: an ADH1 glucose promoter having SEQ ID NO. 1, a snf3 glucose protein receptor having SEQ ID NO. 2, a ribosomal switch having SEQ ID NO. 3, a ribosomal binding site having SEQ ID NO. 4, a terminator having SEQ ID NO. 5, and a reporter protein.

The insulin DNA comprises the following components in the following sequence: an insulin promoter, a human insulin protein, a ribosomal binding site, a terminator, and a reporter protein. In certain aspects, the insulin DNA further comprises a ribosomal switch between the human insulin protein and the ribosomal binding site that can enhance translation and protein expression. Any of the ribosomal switches, ribosomal binding sites, and terminators described above for the glucose DNA can be used to prepare the insulin DNA.

In one aspect, the insulin promoter in the insulin DNA has SEQ ID NO. 7 or a derivative or variant thereof. In another aspect, the human insulin protein in the insulin DNA has SEQ ID NO. 8 or a derivative or variant thereof.

In another aspect, the insulin DNA comprises the following components in the following sequence: an insulin promoter having SEQ ID NO. 7, a human insulin protein having SEQ ID NO. 8, a ribosomal switch having SEQ ID NO. 3, a ribosomal binding site having SEQ ID NO. 4, a terminator having SEQ ID NO. 5, and a reporter protein.

The glucose and insulin DNA can be synthesized using techniques known in the art (see Sandhu et al., Biotechniques, 12, (1992), 14-16). Primers useful for assembling the glucose and insulin DNA include SEQ ID NOS. 9-19. Overlapping primers are assembled and amplified by PCR to provide the full length sequence of the glucose or insulin DNA. The glucose DNA or insulin DNA is then subsequently cloned into the cloning vector (e.g., pYES, PBSKII). Individual clones are then sequenced and site directed mutagenesis was used to correct mutations in the clones and subsequently sequenced for verification. The amount of glucose DNA and insulin DNA incorporated into the vector can vary. In one aspect, the ratio by volume of glucose DNA or insulin DNA to the vector is from 1:1, 1:2, 1:3 1:4, or 1:5. After the vector comprising the glucose DNA or insulin DNA has been produced, the resulting vector can be incorporated into the host cells using the methods described above.

The host cells comprising the glucose and/or insulin DNA described herein are useful as sensors for quantifying the amount of glucose and insulin in a subject. For example, when the host cell comprising the glucose DNA comes into contact with glucose present in a sample, the host cells will produce fluorescent light in an amount proportional to the amount of glucose present. The same principle applies to the insulin sensor (i.e., host cells comprising insulin DNA). The sample to be evaluated can be any biological material that contains glucose or insulin including, but not limited to, blood, serum, plasma, saliva, and urine. Exemplary procedures for contacting the host cells composed of glucose and insulin DNA described herein are provided in the Examples.

The selection of the reporter protein can vary in the glucose and insulin DNA. For example, the reporter protein can be a yellow fluorescent protein, red fluorescent protein, a green fluorescent protein, and a cyan fluorescent protein. In one aspect, the reporter protein has SEQ ID NO. 6. In the case when host cells contain both the glucose DNA and the insulin DNA, the reporter protein is different for each DNA such that the fluorescence that is produced is different and easily detectable. For example, the glucose DNA can have a reporter protein that produces green fluorescent protein when the host cell comes into contact with glucose, and the insulin DNA can have a reporter protein that produces yellow fluorescent protein when the host cell comes into contact with insulin. Here is possible to detect and quantify the amount of green and yellow fluorescence that is produced, which is ultimately used to calculate the amount of glucose and insulin present in the sample. This embodiment is convenient and cost effective, as only one group of host cells and sample are required to measure both glucose and insulin levels.

The fluorescence produced by the host cells can be detected and quantified using techniques known in the art. For example, spectrophotometers are typically used to measure fluorescence. The Examples provide exemplary procedures for measuring the amount of fluorescence as a result of the expression of the glucose DNA or insulin DNA. After the fluorescence has been quantified, the value is correlated in order to provide a glucose or insulin concentration in the sample. In one aspect, the fluorescence value can be directly correlated with the corresponding glucose or insulin results from clinical data. Thus, a chart or computer program can be used to correlate different fluorescence values to different glucose and insulin concentrations. The Examples provide exemplary methods for correlating fluorescence values with clinical data.

The glucose and insulin sensors described herein have numerous clinical applications. For example, they can be used in analytical labs where it is desirable to test many samples. Alternatively, the sensors can be used in the physician's office or at the subject's home in order to evaluate glucose and insulin levels. In one aspect, described herein is a kit comprising (1) a slide comprising the host cells having the glucose and/or insulin DNA for receiving a sample of blood from a subject, and (2) a device for receiving the slide, wherein the device (i) measures the amount of fluorescence produced when the sample comes into contact with the slide and (ii) correlates the amount of glucose and/or insulin present in the sample.

Figure 9:
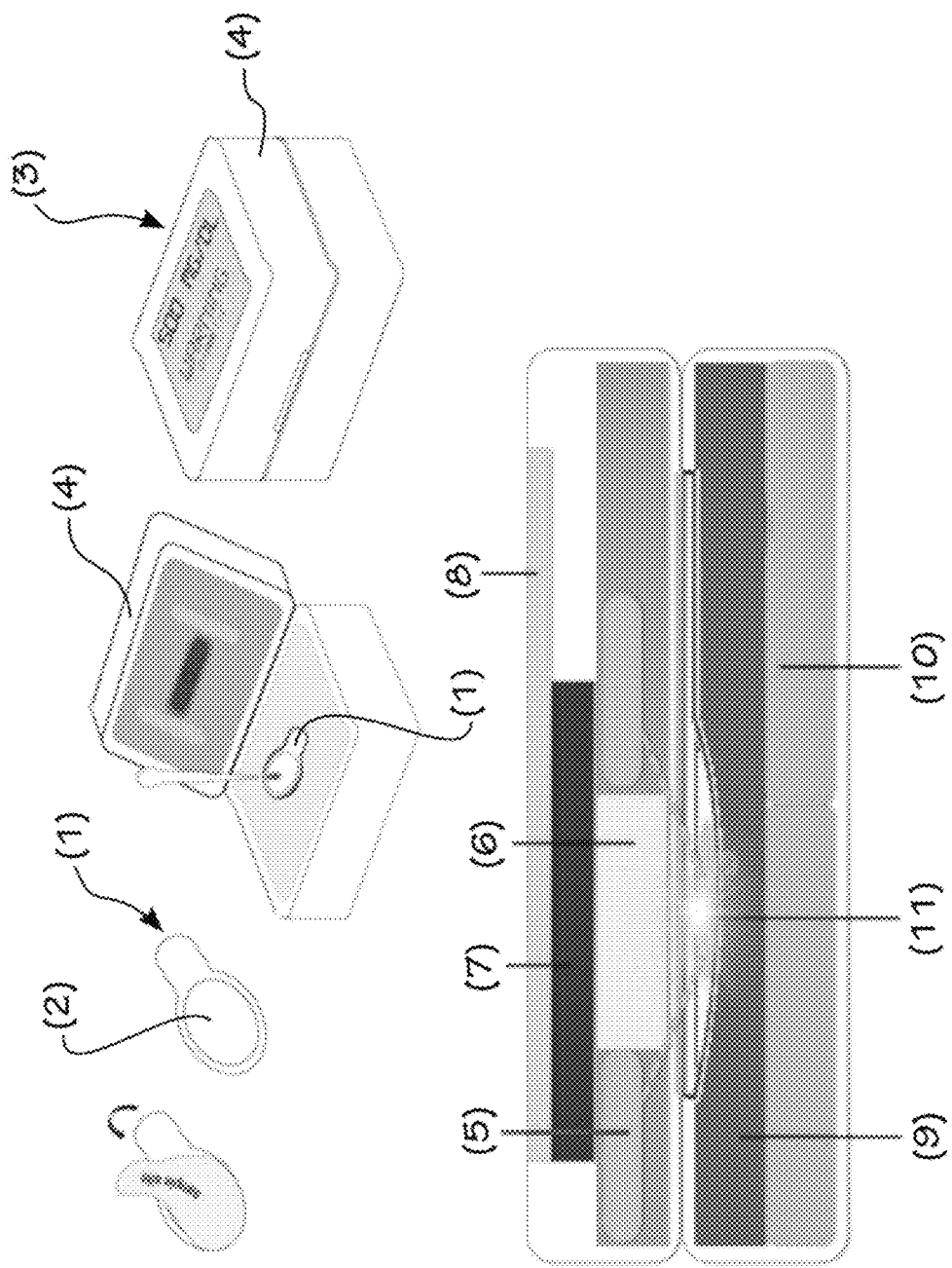
FIG. 9 shows a kit composed of a device and a sensor described herein for use at home or a physician's office.

FIG. 9 depicts an exemplary kit described herein. Slide 1 has on one surface the glucose and/or insulin sensor 2. In one aspect, slide 1 is a disposable concave slide capable of receiving a sample of blood. After a sample of blood is applied to the slide, the slide is placed in a device 3 in sample site 11 that measures the amount of fluorescence produced from the sample on the slide and converts the fluorescence value to a glucose and/or insulin value. Referring to FIG. 9, the lid of the box 4 is fitted with a light source 5 and filter and detector 6 to read fluorescence. A transducer 7 converts the fluorescence values to a digital glucose and/or insulin value that is displayed on screen 8. The device can be fitted with a vibrator 9 in order to ensure that the sample is adequately mixed with the sensor on slide 1. The device can be battery operated for convenience (10 in FIG. 9).

The sensors and methods described herein possess numerous advantages over current glucose and insulin meters. The sensors described herein are able to determine lower levels of glucose (below (<20 mg/dl) than the levels detected by conventional clinical and/or commercial methods. The sensors can measure higher levels of glucose in blood (up to 500 mg/dl), which is comparable to conventional technologies. The sensors can detect a wide range of insulin levels as well (0 to 250 or more µIU/ml). In addition to sensitivity, the sensors described herein can accurately detect different levels of glucose and insulin in blood quicker than current meters available to the public.

The manufacture and use of the sensors is low cost and easy to apply. The sensors are versatile in that they can determine both glucose and insulin in blood simultaneously. This is not the case with technologies, where to different samples and tests are required. The sensors also require a small drop of about 3 µl for analysis. Thus, the sensor can be reused for a longer period of time, which extends the use of the sensor and ultimately reducing costs to the subject.

Due to the higher sensitivity of the sensors, it is possible to differentiate between different stages of diabetes in patients earlier when compared to using conventional methods and technologies. The sensors are designed to be used by physicians and non-physicians in the office or at home with no training involved.

Examples

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Blood Samples.

Samples were taken at different volumes (5,000, 3,000, 1,500, 1,000, 100 and 3 µl) from different individuals, including diabetes, pre-diabetes, and non-diabetic patients. These samples were used immediately and or kept in the refrigerator few minutes until use. Aliquots of 2 ml (amount of blood used) were used for analysis, each time.

Construction of DNA Sensor.

Yeast cells (*Saccharomyces cerevisiae* ATCC 200892) were transformed to be able to hold the new synthesized DNA genetic parts assembled in plasmid vectors (genetic parts sequences such as glucose ADH1 promoter, snf3 glucose receptor, insulin promoter, insulin protein, riboswitch tc aptamer, and different reporter protein such as cyanin, Red and yellow Fluorescent proteins to produce differential fluorescent gene expression based on glucose and insulin concentrations, and also to ensure assembly, and pYES plasmid as backbone or vector). The methods disclosed in Leonard G. Davis, Michael Kuehl, James F. Battey. 1995. Basic Methods In Molecular Biology. McGraw-Hill Professional; 2nd edition, and Gietz, R. D. and R. H. Schiestl. 2007. Nature Protocols. Quick and easy yeast transformation using the LiAc/SS carrier DNA/PEG method. Vol 2. 35-37. doi:10.1038/nprot.2007.14 were used to transform the yeast with the DNA.

Two different types of sensors, one for glucose and one for insulin in blood, were constructed, as follows:

SENSOR FOR INSULIN IN BLOOD. The sensor for detection of insulin in blood, was constructed by assembling plasmid including parts sequences of Insulin promoter (401 bps), Human insulin protein (333 bps) and ribosomal switch (76 bps), Ribosomal Biding Site (RBS, 29 bps), Terminator (129 bps) and reporter protein (979 bps) that produces fluorescence.

SENSOR FOR GLUCOSE IN BLOOD. The sensor was constructed to determine the concentration of glucose in blood. Different gene parts and proteins, include plasmid (pBSKII), sequences of ADH1 glucose promoter (1445 bps), snf3 glucose protein receptor (2244 bps) and ribosomal switch (76 bps), Ribosomal Biding Site (RBS, 29 bps), Terminator (129 bps) and reporter protein (979 bps) that produce fluorescence.

Two different transformed yeast cells (i.e., DNA sensors) were obtained. Different types of reporter fluorescent proteins were used (yellow fluorescent protein, red Fluorescent protein, green fluorescent protein and cyan fluorescent protein) for all transformed yeast cells or devices. However, the cyan fluorescent protein was the best to express the fluorescence (mostly green or light blue in color). When no reporter fluorescent protein was assembled no fluorescence was observed. (Tables 1 and 2).

In this protocol, PCR was used to enhance DNA concentration using standard 5332 eppendorf thermocycler (Eppendorf North America. 102 Motor Parkway, Hauppauge, N.Y. 11788) with specific sequence primers (SEQ ID NOS. 9-19), and the standard method for amplification (Sambrook et. al, 1989); digestion and ligation were used to ensure assembly of DNA synthesized parts using promega restriction enzymes and reagents (promega PCR master mix, restriction enzymes: XhoI, KpnI, XbaI EcoRI, BamHI and HindII, Alakaline Phosphatase and quick ligation kit among others). DNA was quantified using a nano view spectrophotometer GE nanospectrophotometer (GE Healthcare Biosciences P.O. Box 643065 Pittsburgh, Pa. 15264-3065), and also regular standard UV/visual spectrophotometer within a 260/280 wavelength (GE Healthcare Biosciences P.O. Box 643065 Pittsburgh, Pa. 15264-3065), to verify final ligations. DNA was visualized and purified with electrophoresis using standard Thermo EC (EC-150) electrophoresis equipment.

Figure 2:
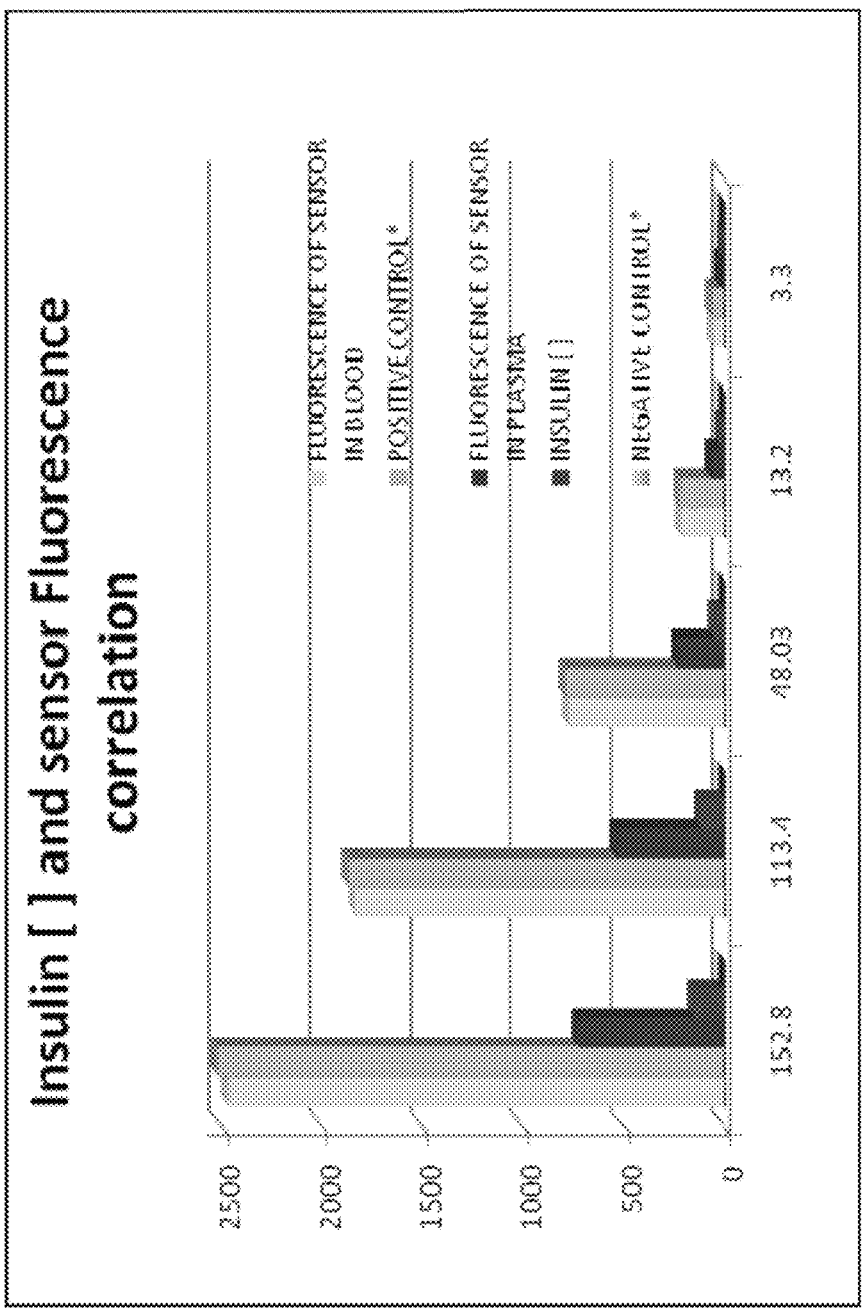
FIG. 2 shows (A) the equivalent proportion correlation of sensor fluorescence and clinical insulin values; and (B) the equivalent proportion correlation of the DNA sensor and fluorescence when testing for insulin in different patients including uncontrolled diabetic, controlled diabetic, pre-diabetic, non diabetic and hypoglycemic patients.
Figure 2:
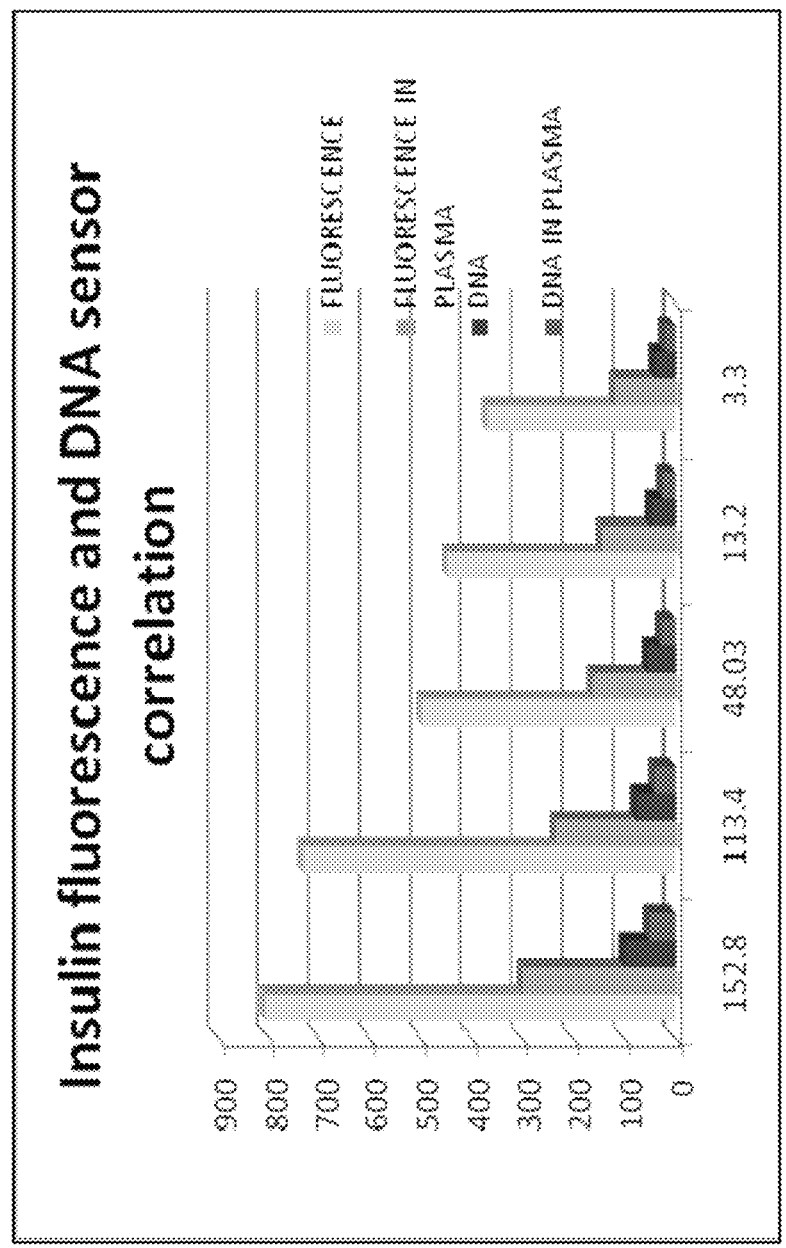
Figure 3:
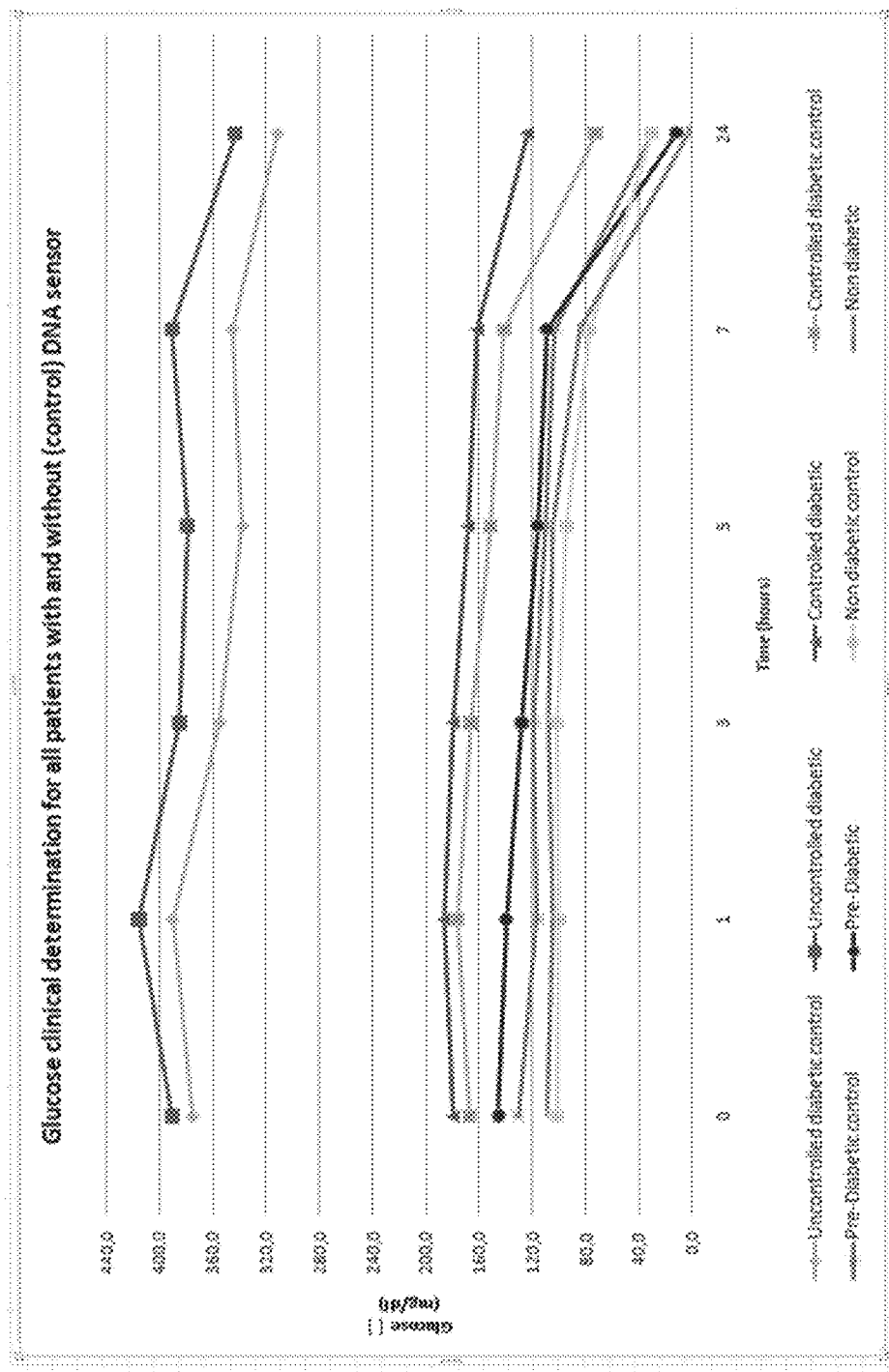
FIG. 3 shows the sensibility of a sensor described herein in comparison with conventional methods (differences in the ability to measure clinical glucose, in different diabetic and non-diabetic patients within 24 hours).
Figure 4:
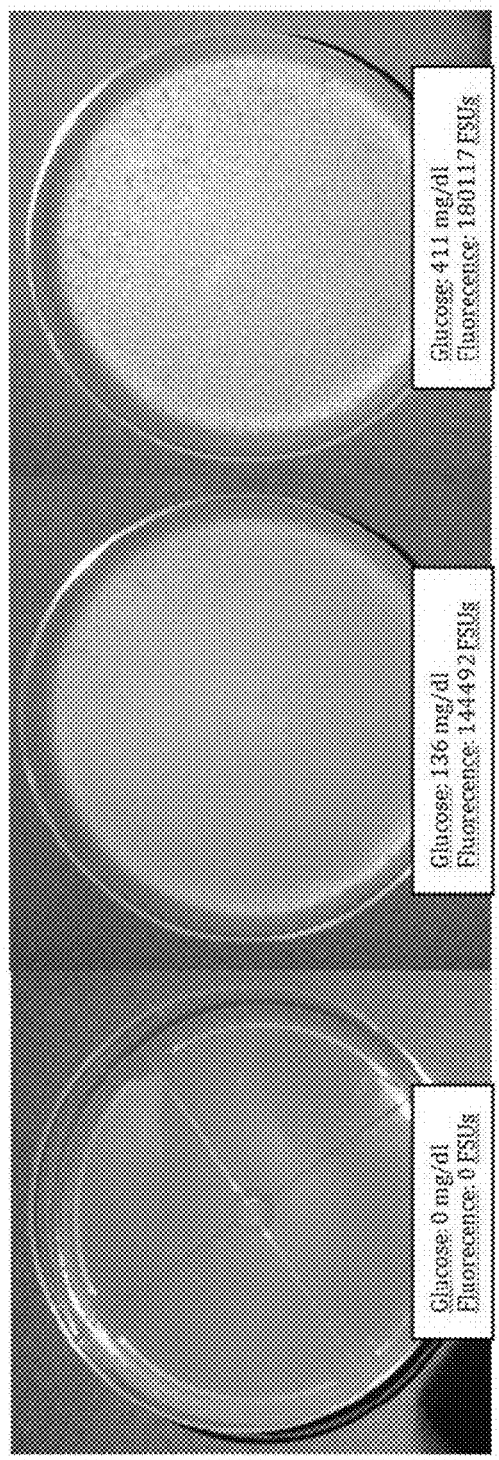
FIG. 4 shows a yeast device sensor with colonies fluorescing after exposure to different glucose concentrations in vitro assay.
Figure 5:
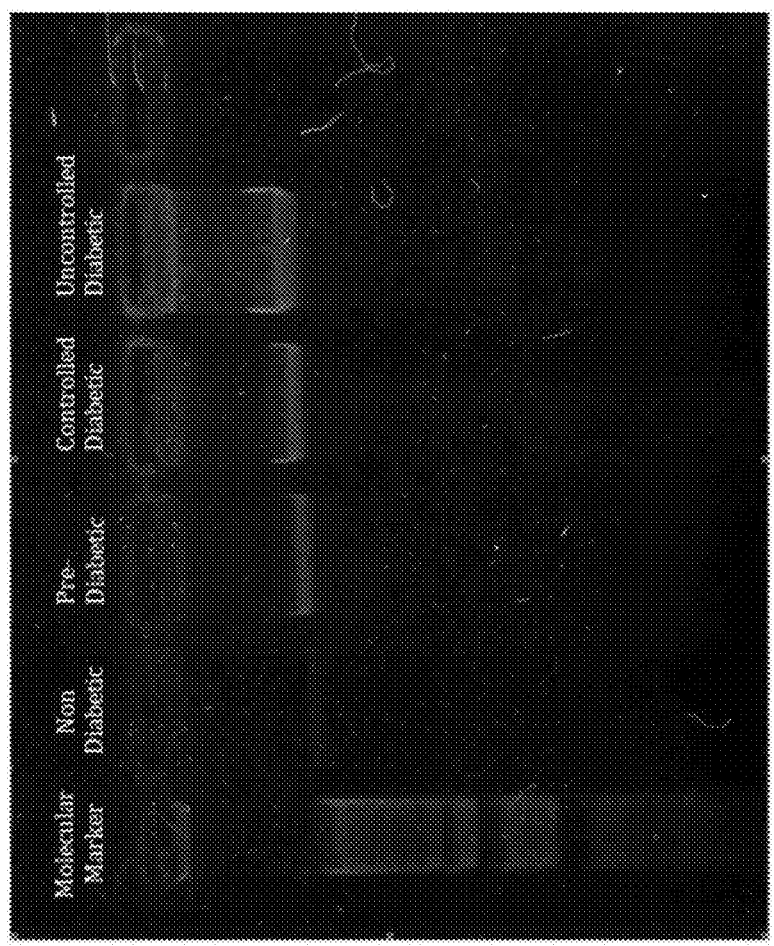
FIG. 5 shows the electrophoresis bands of a sensor described herein, expressing different fluorescence after exposure to blood samples from different patients. In vivo test. The bans in the gel indicate the following from left to right. Lane 1. Molecular DNA marker (1 Kb). Lane 2. Sensor described herein expressed in normal patient sample. Lane 3. Sensor described herein expressed in Pre-diabetic patient sample. Lane 4. Sensor described herein expressed in controlled diabetic patient sample. Lane 5. Sensor described herein expressed in uncontrolled diabetic patient sample.

DNA expression was determined by fluorescence of the transformed cells expressed in Florescent units (FSUs) according the company protocol using the promega 20/20 illuminometer, with the blue fluorescence module within the 450/600 wave length. The DNA sensor was only fluorescent in blood when the transformed yeast cells or device contained the denoted parts and plasmids that were specific for glucose or insulin, as compared to control non-transformed yeast cells that do not contain the glucose or insulin DNA (Tables 1 and 2 and FIG. 5). The direct relationship between sensitivity of the DNA sensor and fluorescence with glucose or insulin concentrations was also demonstrated (FIGS. 1B and 2B). The efficacy of the sensor was assayed in vitro in an agar plate and liquid broth where the transformed yeast cells were growing (FIG. 4) and in vivo, using blood drop and other volume samples, in which the fluorescence was determined based on the concentration of glucose and insulin (FIGS. 1 and 2).

TABLE 1

Differential DNA sensor fluorescence and DNA determinations based on clinical glucose concentration for different types of diabetic patients. Uncontrolled diabetic, controlled diabetic, pre-diabetic, non-diabetic and hypoglycemic patients.

| Patient | Fluorescence (FSUs) | Glucose (mg/dl) | DNA (ng/µl) |
| --- | --- | --- | --- |
| Uncontrolled diabetic | 180117 ± 2069.5 | 411 ± 3.5 | 85 ± 4.8 |
| Uncontrolled diabetic control* | 0 | 387 ± 2.9 | 25 ± 0 |
| Uncontrolled diabetic plasma | 90647 ± 542 | 411 ± 3.5 | 30.7 ± 1.3 |
| Controlled diabetic | 174512.8 ± 3532.5 | 185.7 ± 1.9 | 77 ± 1.1 |
| Controlled diabetic control* | 0 | 178.2 ± 2.5 | 11.5 ± 2.3 |
| Controlled diabetic plasma | 88135 ± 1204 | 185.7 ± 1.9 | 23.7 ± 2.4 |
| Pre-diabetic | 144492.4 ± 709 | 135.9 ± 5.1 | 52.5 ± 2.6 |
| Pre-diabetic control* | 0 | 122.4 ± 2.1 | 23 ± 1.6 |
| Pre-diabetic plasma | 76328 ± 784 | 135.9 ± 5.1 | 16.15 ± 1.5 |
| Non diabetic | 115409.4 ± 540.7 | 107.1 ± 5.3 | 47 ± 0.6 |
| Non diabetic control* | 0 | 100.2 ± 3.1 | 18.5 ± 0.6 |
| Non diabetic plasma | 58439 ± 2131 | 107.1 ± 5.3 | 14.5 ± 1 |
| Hypoglicemic | 79917 ± 3066.3 | 12.5 ± 3.1 | 39 ± 7.1 |
| Hypoglicemic control* | 0 | <20 ± 0 | 15.4 ± 3.1 |
| Hypoglycemic plasma | 37194 ± 341 | 12.5 ± 3.1 | 12 ± 0.7 |

*Control: patient sample with no sensor device (water instead) or no fluorescent reporter protein assembled to it.

TABLE 2

Differential DNA sensor fluorescence and DNA determinations based on clinical Insulin concentration for different types of diabetic patients. Uncontrolled diabetic, controlled diabetic, pre-diabetic, non-diabetic and hypoglycemic patients.

| Patient | Fluorescence (FSUs) | Insulin (µIU/ml) | DNA (ng/µl) |
| --- | --- | --- | --- |
| Uncontrolled diabetic | 334121.6 ± 3811.9 | 48.03 ± 1.4 | 85 ± 4.8 |
| Uncontrolled diabetic control* | 0 | 48.03 ± 1.4 | 25 ± 0 |
| Uncontrolled diabetic plasma | 85371 ± 1532 | 48.03 ± 1.4 | 36.5 ± 2 |
| Controlled diabetic | 378019 ± 3981.6 | 152.8 ± 0.3 | 77 ± 1.1 |
| Controlled diabetic control* | 0 | 152.8 ± 0.3 | 11.5 ± 2.3 |
| Controlled diabetic plasma | 97328 ± 903 | 152.8 ± 0.3 | 27.3 ± 0.8 |
| Pre-diabetic | 337661.8 ± 4711.1 | 113.4 ± 0.1 | 52.5 ± 2.6 |
| Pre-diabetic control* | 0 | 113.4 ± 0.1 | 23 ± 1.6 |
| Pre-diabetic plasma | 92186 ± 1137 | 113.4 ± 0.1 | 18.9 ± 1.2 |
| Non diabetic | 210546.7 ± 2093.7 | 3.3 ± 1.2 | 47 ± 0.6 |
| Non diabetic control* | 0 | 3.3 ± 1.2 | 18.5 ± 0.6 |
| Non diabetic plasma | 27328 ± 2231 | 3.3 ± 1.2 | 15.2 ± 1.3 |
| Hypoglicemic | 275659 ± 629.8 | 13.2 ± 0.4 | 39 ± 7.1 |
| Hypoglicemic control* | 0 | 13.2 ± 0.4 | 15.4 ± 3.1 |
| Hypoglycemic plasma | 60397 ± 395 | 13.2 ± 0.4 | 11.3 ± 0.3 |

*Control: patient sample with no sensor device (water instead) or no fluorescent reporter protein assembled to it.

In Vitro Yeast Growth and DNA Detection of Glucose and Insulin in Culture Media.

Yeast cells were grown in YPD commercial media from 8 to 18 hours until they reached an OD of 1. They were sub-cultured in sterile-deionized water in different glucose blood equivalent concentrations (from 0 to 500 mg/dl) and or different proportion of insulin (1:1, 1:2, 1:3, 1:4, 0:1) during different time intervals ranging from 1 hour to 48 hours. Fluorescence and DNA were determined for all samples and correlated with glucose and insulin concentrations (FIGS. 1B and 2B). The fluorescence is provided in FSUs according to the protocol of the company 20/20 promega fluorometer.

The In Vivo Determinations of Glucose and Insulin.

Figure 6:
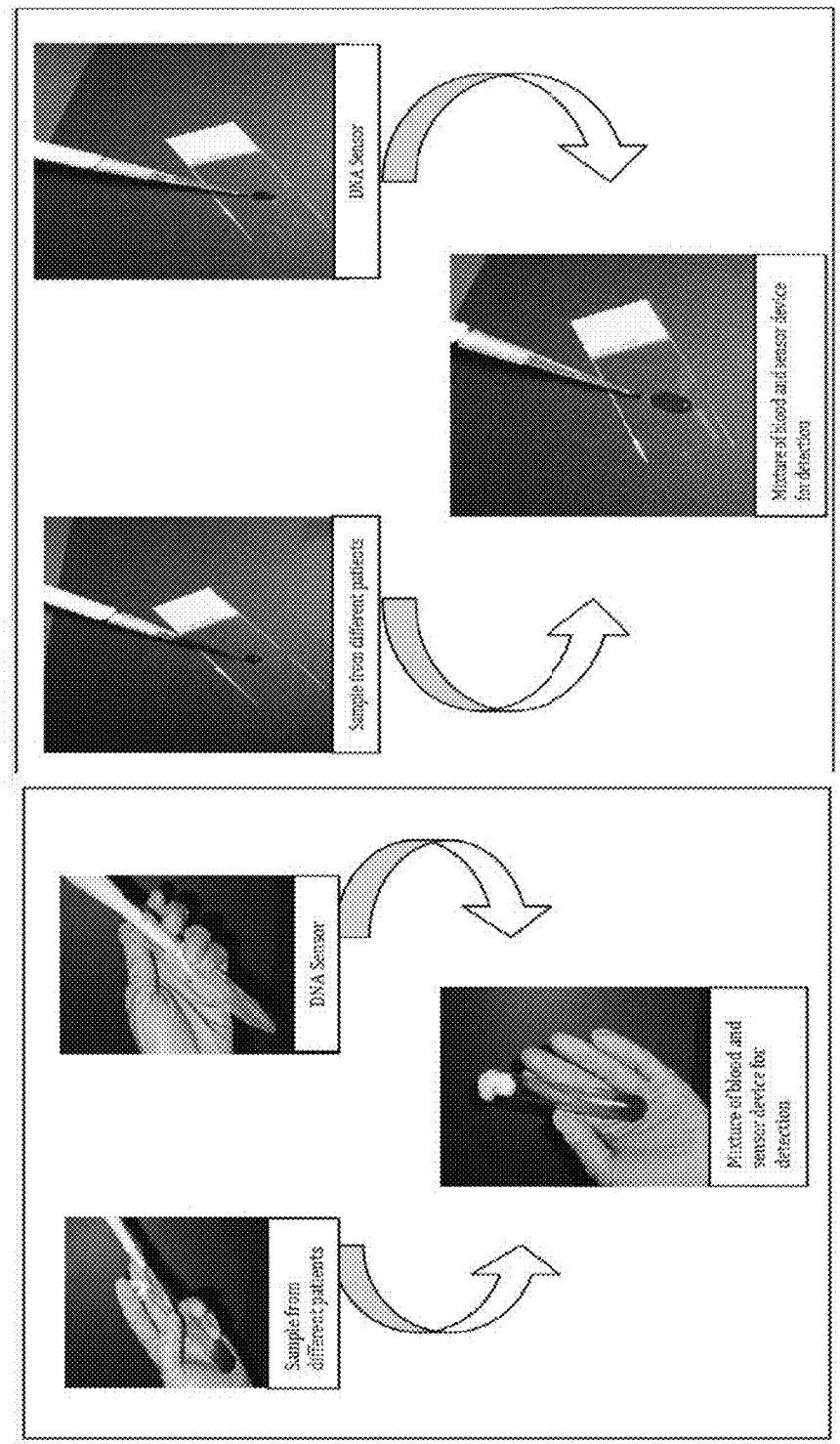
FIG. 6 shows steps for preparing blood samples for glucose and or insulin detention after mixed with the sensor described herein indicating the process for preparing the analysis of glucose and or insulin mixed with the sensor for detection. Time course experiments showed no blood alteration after mixing with the sensor.

Blood samples obtained from patients as described above were mixed with the glucose or insulin DNA sensor with an initial concentration of 10*3 cells (Optical Density: 0.09). The mixture was mixed and vortexed very lightly (15 rpm) for different times in order to ensure full mixture (FIG. 6). Different levels of fluorescence were produced from this mixture depending on the concentration of glucose and insulin (e.g. from 12 to 450 mg/dl for glucose and from 3 to 150 μIU/ml for insulin, Tables 1 and 2), at different times (30, 5, 3 and 1 minutes and 24, 12, 7, 5, 3, 1 hours), with 1 minute was the preferred time. This fluorescence is provided in FSUs according to the protocol of the company 20/20 promega fluorometer.

The results are presented by the mean with the respective standard deviation, 4 replicates of blood sample for each treatment were used each time in order to have reliable statistical analysis. The statistical analysis was based on the program SigmaPlot-Scientific Data Analysis and Graphing Software. The results are expressed as mean and standard deviation and difference within treatments, and with an a of 0.005.

Glucose and insulin values for all samples were determined by glucose oxidation method and electrochemiluminescence, respectively. The blood samples for insulin detection by the DNA sensor were also subjected to clinical analysis in the Hormonal Research Laboratory in Bogota, Colombia. The concentration of insulin obtained from this laboratory was compared to the concentration of insulin obtained from the fluorescence of the yeast DNA sensor mixed with the blood samples. Blood samples not mixed with the DNA sensor were the control. Other controls included the DNA sensor mixed with sterile-deionized water or with blood plasma. There was no fluorescence in the mixture of the DNA sensor with water. Some fluorescence, approximately half of the produced in blood or pure solutions of glucose and insulin was observed, which showed similar proportions in the mixture of the DNA sensor and the plasma (Figures and Tables 1 and 2). The fluorescence units were directly correlated with the corresponding glucose or insulin results from the clinical data. It represents the expression of the reporter protein assembled in the different plasmid parts of the DNA sensor.

Analysis of Protein Expression in Yeast.

Figure 7:
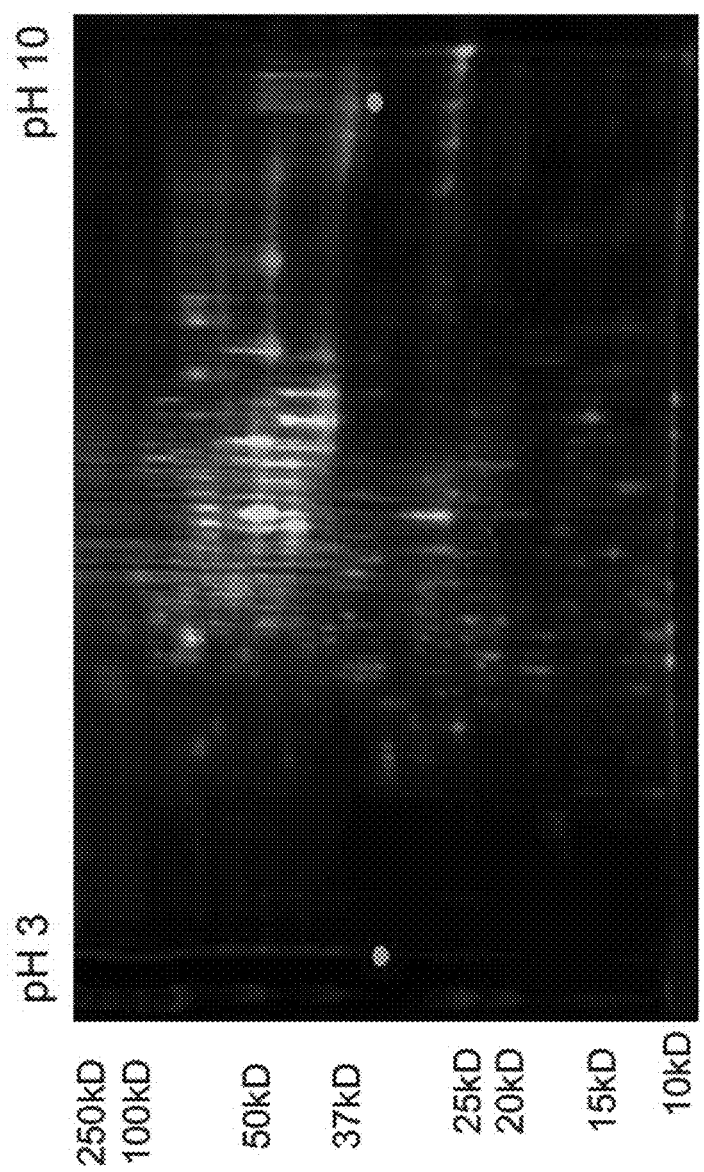
FIG. 7 shows two dimensional (2D-DIGE) gel showing fluorescence of the proteins produced by the sensor described herein at different intensities. The brightest spots were selected for analysis under HPLC mass spectrometry and laser identification.
Figure 8:
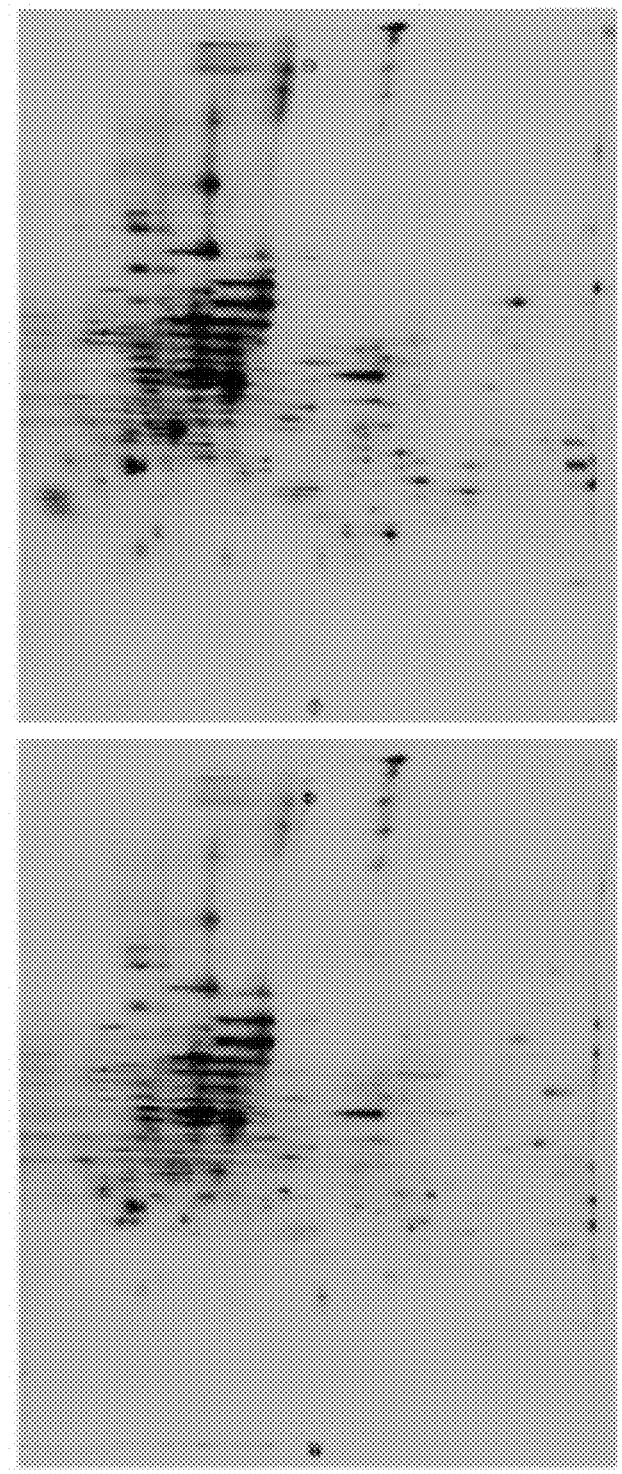
FIG. 8 shows different protein spots selected from the brightest protein spot, after using laser beams. The control gel (no transformed yeast) is in the left of the transformed gel. In the control gel, there are down-regulated proteins, and on the right gel the transformed or treated yeast gel the up-regulated proteins. The proteins are expressed by the degree of intensity. Experimental gel (DNA sensor) shows the brightest spots.

The difference in expression can be seen in the 2D DIGE gels shown in FIG. 7. Six spots of each representing increased or decreased amount of protein from the gels were analyzed and identified. Eight of the identified proteins are shown in a Table 3. It was observed that nucleotides and amino acids were synthesized. Proteins were regulated and expressed in higher concentrations of glucose and insulin.

TABLE 3

List of main proteins produced by the Sensor devices after MALDI, LASER and HPLC mass spectrometry analysis. Identification of protein spots showing changes in protein expression. Production of the proteins confirmed that the transformed sensor device was prepared properly, and the assemblage of the different genetic components occurred effectively.

| Spot No. | Name | Accession No. | Change | Volume ratio (fold) | Description |
|---|---|---|---|---|---|
| 1225 | S-adenosylmethionine synthase 2 | P19358.3 | Increased | 3 | Catalyzes the formation of S-adenosylmethionine from methionine and ATP. Amynoacid byosinthesys. Glucose and insulin increased cellular homocysteine production primarily by its inhibition of transsulfuration |
| 1061 | Pyruvate kinase 1 | P00549.2 | Increased | 3 | Involved in glycolysis. It catalyzes the transfer of a phosphate group from phosphoenolpyruvate (PEP) to ADP, yielding one molecule of pyruvate and one molecule of ATP |
| 1843 | Phosphomannomutase | P07283.1 | Increased | 3 | Transfer of phosphate groups within a molecule. D-glucose 1,6-bisphosphate cofactor dependent. Phosphoglucomutase activity in some tissues |
| 1568 | Protein disulfide isomerase | P17505.2 | Increased | 2 | Catalyzes the formation and breakage of disulfide bonds between cysteine residues within proteins as they fold. Glucose regulated proteins |
| 1126 | Hexokinase 1 | P04806.2 | Increased | 7 | phosphorylates a six-carbon sugar, to a hexose phosphate. Glucose is the most important substrate of hexokinases, and glucose-6-phosphate is the product |
| 1923 | Translationally-controlled tumor protein analog (TCTP | P3569.1 | Increased | 8 | Anti-apoptotic protein. May contribute to explain the different effects exerted by palmitate and oleate on β-cell function. Inhibiting down-regulation of enzymes of glycolysis |

TABLE 3-continued

List of main proteins produced by the Sensor devices after MALDI, LASER and HPLC mass spectrometry analysis. Identification of protein spots showing changes in protein expression. Production of the proteins confirmed that the transformed sensor device was prepared properly, and the assemblage of the different genetic components occurred effectively.

| Spot No. | Name | Accession No. | Change | Volume ratio (fold) | Description |
|---|---|---|---|---|---|
| 803 | Glutamate synthase | Q12680.2 | Decreased | 14 | Participates in glutamate metabolism and nitrogen metabolism. In S. cerevisiae. Glucose exerts strong catabolite repression on the enzymes required for respiration and on the enzymes of the tricarboxylic acid cycle beyond those required for the synthesis of 2-ketoglutarate. It occurs in bacteria and plants but not animals |
| 575 | Glycinamide ribonucleotide synthetase | P07244.1 | Decreased | 9.05 | De novo purIn biosynthesis. Inhibited when high levels of adoMet are present possibly due to phosphate produced during enzyme reaction. |

Analysis Cost Estimation.

Cost per sample was estimated, including depreciated value of equipment, cost of materials required to take the sample, and price of reagents in the sensor. The cost per sample is based on statistical values of 700 samples monthly for glucose and 500 for insulin including measurement of reference and standards daily, downtime and equipment capacity.

Both apparatuses in the case of the glucose sensor are considered manual. In both cases, one can afford on semi and automated equipment, which is more expensive but can create more capacity for sampling and lowering the price per sample. The biggest difference for glucose analysis is in the use of two apparatuses for the conventional method and material costs required to take and store the sample (Table 4). In the case of the insulin cost analysis, the cost of reagents makes a big difference in determining price per sample (Table 5).

TABLE 4

Cost of glucose analysis without utility using the glucose sensor in comparison to existing technology in the market.

|  | Cost analysis/sample/person in clinical laboratories | Cost analysis/sample/person in personal or home monitoring methods |
|---|---|---|
| DNA sensor | $0.5 USD | $0.5 USD |
| Conventional analysis | $1.3 USD | $0.4-1 USD |

TABLE 5

Cost of insulin analysis without utility using the insulin sensor in comparison to existing technology in the market.

|  | Cost analysis/sample/person in clinical laboratories | Cost analysis/sample/person in personal or home monitoring methods |
|---|---|---|
| DNA sensor | $0.5 USD | $0.5 USD |
| Conventional analysis | $11.15 USD | N.A* |

*Not available. No knowledge of its existence

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A host cell comprising a DNA construct comprising (a) a gene that expresses an alcohol dehydrogenase 1 (ADH1) promoter having at least 95% homology to SEQ ID NOS 1 or 30-32, (b) a gene that expresses snf3 protein having at least 95% homology to SEQ ID NOS 2 or 20-29, and (c) a ribosomal switch.

2. The host cell of claim 1, wherein the host cell comprises yeast or *E. coli*.

3. The host cell of claim 1, wherein the DNA construct comprises a vector.

4. The host cell of claim 3, wherein the vector is pWL-NEO, pSV2CAT, pOG44, PXT1, pSG, pSVK3, pBSK, pBR322, pYES, PBSKII, or a pUC vector.

5. The host cell of claim 1, wherein the DNA construct comprises a plasmid.

6. The host cell of claim 1, wherein the gene that expresses the ADH1 promoter has at least 95% homology to SEQ ID NO 1, the gene that expresses snf3 protein has at least 95% homology to SEQ ID NO 2, and ribosomal switch.

7. A host cell comprising a DNA construct comprising (a) a gene that expresses an alcohol dehydrogenase 1 (ADH1) promoter having at least 95% homology to SEQ ID NOS 1 or 30-32 and (b) a gene that expresses snf3 protein having at least 95% homology to SEQ ID NOS 2 or 20-29, wherein the construct comprises a vector, wherein the vector is pWLNEO, pSV2CAT, pOG44, PXT1, pSG, pSVK3, pBSK, pBR322, pYES, PBSKII, or a pUC vector.

8. The host cell of claim 7, wherein the DNA construct further comprises a ribosomal switch.

9. The host cell of claim 7, wherein the host cell comprises yeast or *E. coli*.

10. The host cell of claim 7, wherein the gene that expresses the ADH1 promoter has at least 95% homology to SEQ ID NO 1, the gene that expresses snf3 protein has at least 95% homology to SEQ ID NO 2, and ribosomal switch.

* * * * *